United States Patent
Beasley

(10) Patent No.: US 10,092,725 B2
(45) Date of Patent: Oct. 9, 2018

(54) RESOURCE INFORMATION KEY FOR AN INSERTABLE MEDICAL DEVICE

(71) Applicant: C. R. Bard, Inc., Murray Hill, NJ (US)

(72) Inventor: Jim C. Beasley, Houston, TX (US)

(73) Assignee: C. R. Bard, Inc., Murray Hill, NJ (US)

( * ) Notice: Subject to any disclaimer, the term of this patent is extended or adjusted under 35 U.S.C. 154(b) by 0 days.

(21) Appl. No.: 15/585,030

(22) Filed: May 2, 2017

(65) Prior Publication Data

US 2017/0232232 A1    Aug. 17, 2017

Related U.S. Application Data

(62) Division of application No. 11/937,302, filed on Nov. 8, 2007, now Pat. No. 9,642,986.

(60) Provisional application No. 60/864,806, filed on Nov. 8, 2006.

(51) Int. Cl.
*A61M 25/01* (2006.01)
*A61M 25/06* (2006.01)
*A61M 25/00* (2006.01)

(52) U.S. Cl.
CPC ........ *A61M 25/01* (2013.01); *A61M 25/0606* (2013.01); *A61M 2025/0008* (2013.01)

(58) Field of Classification Search
CPC .......... A61M 2025/0008; A61M 25/01; A61M 25/0606
See application file for complete search history.

(56) References Cited

U.S. PATENT DOCUMENTS

| | | | |
|---|---|---|---|
| 445,896 | A | 2/1891 | Kinsman |
| 546,440 | A | 9/1895 | Tufts |
| 574,387 | A | 1/1897 | Buckler |
| 611,357 | A | 9/1898 | Dembinski |

(Continued)

FOREIGN PATENT DOCUMENTS

| | | |
|---|---|---|
| AU | 2008299945 A1 | 3/2009 |
| CA | 2663853 A1 | 4/2008 |

(Continued)

OTHER PUBLICATIONS

U.S. Appl. No. 12/796,133, filed Jun. 8, 2010 Non-Final Office Action dated Feb. 17, 2011.

(Continued)

*Primary Examiner* — Imani Hayman
(74) *Attorney, Agent, or Firm* — Rutan & Tucker, LLP

(57) ABSTRACT

A system by which resource information relating to an insertable medical device, such as an intravascular catheter, can be identified by its source so as to be accessed by a practitioner, caregiver, or patient, is disclosed. In particular, a resource information key is included at a predetermined key location on or proximate to the medical device, wherein the key indicates the source of the resource information. In one example embodiment, therefore, an insertable medical device for establishing intravascular access to a patient, such as a peripherally inserted central catheter ("PICC"), is disclosed and comprises: an internal portion configured for intravascular insertion into the patient, and a portion external to the patient. The exterior portion of the PICC includes a resource information key that is positioned at a predetermined key location. The resource information key indicates a website where a user can acquire the resource information relating to the medical device.

6 Claims, 6 Drawing Sheets

(56) References Cited

U.S. PATENT DOCUMENTS

| | | |
|---|---|---|
| 966,696 A | 8/1910 | Merrill |
| D44,302 S | 7/1913 | Director |
| 1,713,267 A | 5/1929 | Crowley |
| D130,852 S | 12/1941 | Rothschild |
| 2,433,480 A | 12/1947 | Rendich |
| 2,891,689 A | 6/1959 | Gould |
| 3,159,175 A | 12/1964 | Macmillan |
| 3,211,431 A | 10/1965 | Meysembourg et al. |
| 3,293,663 A | 12/1966 | Cronin |
| 3,341,417 A | 9/1967 | Sinaiko |
| 3,477,438 A | 11/1969 | Allen et al. |
| 3,518,428 A | 6/1970 | Ring |
| 3,525,357 A | 8/1970 | Koreski |
| 3,529,633 A | 9/1970 | Vaillancourt |
| 3,540,670 A | 11/1970 | Rissberger |
| 3,643,358 A | 2/1972 | Morderosian |
| 3,669,323 A | 6/1972 | Harker et al. |
| 3,674,183 A | 7/1972 | Venable et al. |
| 3,811,466 A | 5/1974 | Ohringer |
| 3,829,904 A | 8/1974 | Ling et al. |
| 3,831,549 A | 8/1974 | Parsons |
| 3,831,583 A | 8/1974 | Edmunds, Jr. et al. |
| 3,840,009 A | 10/1974 | Michaels et al. |
| 3,853,127 A | 12/1974 | Spademan |
| 3,891,997 A | 7/1975 | Herbert |
| 3,915,162 A | 10/1975 | Miller |
| 3,919,724 A | 11/1975 | Sanders et al. |
| 3,922,726 A | 12/1975 | Trentani et al. |
| 3,951,147 A | 4/1976 | Tucker et al. |
| 3,955,594 A | 5/1976 | Snow |
| 3,971,376 A | 7/1976 | Wichterle |
| 4,027,391 A | 6/1977 | Samis |
| 4,035,653 A | 7/1977 | Karasko |
| 4,121,108 A | 10/1978 | Manor |
| 4,123,806 A | 11/1978 | Amstutz et al. |
| 4,143,853 A | 3/1979 | Abramson |
| 4,168,586 A | 9/1979 | Samis |
| 4,181,132 A | 1/1980 | Parks |
| 4,190,040 A | 2/1980 | Schulte |
| 4,190,057 A | 2/1980 | Hill et al. |
| 4,194,122 A | 3/1980 | Mitchell et al. |
| 4,196,731 A | 4/1980 | Laurin et al. |
| 4,202,349 A | 5/1980 | Jones |
| 4,222,374 A | 9/1980 | Sampson et al. |
| 4,233,964 A | 11/1980 | Jefferts et al. |
| 4,274,006 A | 6/1981 | Caine |
| D263,335 S | 3/1982 | Bujan |
| 4,349,498 A | 9/1982 | Ellis et al. |
| 4,361,153 A | 11/1982 | Slocum et al. |
| 4,405,305 A | 9/1983 | Stephen et al. |
| 4,406,567 A | 9/1983 | Samis |
| 4,425,119 A | 1/1984 | Berglund |
| 4,445,896 A | 5/1984 | Gianturco |
| 4,447,237 A | 5/1984 | Frisch et al. |
| 4,450,592 A | 5/1984 | Niederer et al. |
| 4,450,985 A | 5/1984 | Beard |
| 4,456,011 A | 6/1984 | Warnecke |
| 4,469,483 A | 9/1984 | Becker et al. |
| 4,479,798 A | 10/1984 | Parks |
| 4,494,545 A | 1/1985 | Slocum et al. |
| 4,506,676 A | 3/1985 | Duska |
| 4,529,635 A | 7/1985 | Sheldon |
| 4,543,088 A | 9/1985 | Bootman et al. |
| 4,549,879 A | 10/1985 | Groshong et al. |
| 4,559,043 A | 12/1985 | Whitehouse et al. |
| 4,559,046 A | 12/1985 | Groshong et al. |
| 4,560,375 A | 12/1985 | Schulte et al. |
| 4,569,675 A | 2/1986 | Prosl et al. |
| 4,571,749 A | 2/1986 | Fischell |
| 4,576,595 A | 3/1986 | Aas et al. |
| 4,610,665 A | 9/1986 | Matsumoto et al. |
| 4,612,877 A | 9/1986 | Hayes et al. |
| 4,626,244 A | 12/1986 | Reinicke |
| 4,627,844 A | 12/1986 | Schmitt |
| 4,634,427 A | 1/1987 | Hannula et al. |
| 4,636,194 A | 1/1987 | Schulte et al. |
| 4,636,213 A | 1/1987 | Pakiam |
| 4,645,495 A | 2/1987 | Vaillancourt |
| 4,653,508 A | 3/1987 | Cosman |
| 4,655,765 A | 4/1987 | Swift |
| 4,657,024 A | 4/1987 | Coneys |
| 4,662,652 A | 5/1987 | Hargis |
| 4,668,221 A | 5/1987 | Luther |
| 4,671,796 A | 6/1987 | Groshong et al. |
| 4,673,394 A | 6/1987 | Fenton, Jr. et al. |
| 4,681,560 A | 7/1987 | Schulte et al. |
| 4,684,365 A | 8/1987 | Reinicke |
| 4,685,447 A | 8/1987 | Iversen et al. |
| 4,685,905 A | 8/1987 | Jeanneret nee Aab |
| 4,692,146 A | 9/1987 | Hilger |
| 4,695,273 A | 9/1987 | Brown |
| 4,697,595 A | 10/1987 | Breyer et al. |
| 4,701,166 A | 10/1987 | Groshong et al. |
| 4,704,103 A | 11/1987 | Stober et al. |
| 4,707,389 A | 11/1987 | Ward |
| 4,710,167 A | 12/1987 | Lazorthes |
| 4,710,174 A | 12/1987 | Moden et al. |
| 4,718,894 A | 1/1988 | Lazorthes |
| 4,723,947 A | 2/1988 | Konopka |
| 4,728,894 A | 3/1988 | Yoda et al. |
| 4,743,231 A | 5/1988 | Kay et al. |
| 4,753,640 A | 6/1988 | Nichols et al. |
| 4,755,173 A | 7/1988 | Konopka et al. |
| 4,760,837 A | 8/1988 | Petit |
| 4,762,517 A | 8/1988 | McIntyre et al. |
| 4,767,410 A | 8/1988 | Moden et al. |
| 4,772,270 A | 9/1988 | Wiita et al. |
| 4,772,276 A | 9/1988 | Wiita et al. |
| 4,773,552 A | 9/1988 | Boege et al. |
| 4,778,452 A | 10/1988 | Moden et al. |
| 4,781,680 A | 11/1988 | Redmond et al. |
| 4,781,685 A | 11/1988 | Lehmann et al. |
| 4,781,695 A | 11/1988 | Dalton |
| 4,784,646 A | 11/1988 | Feingold |
| 4,793,635 A | 12/1988 | Lovison |
| 4,802,885 A | 2/1989 | Weeks et al. |
| 4,804,054 A | 2/1989 | Howson et al. |
| 4,820,273 A | 4/1989 | Reinicke |
| 4,822,341 A | 4/1989 | Colone |
| 4,840,615 A | 6/1989 | Hancock et al. |
| 4,848,346 A | 7/1989 | Crawford |
| 4,857,053 A | 8/1989 | Dalton |
| 4,861,341 A | 8/1989 | Woodburn |
| 4,863,470 A | 9/1989 | Carter |
| 4,886,501 A | 12/1989 | Johnston et al. |
| 4,886,502 A | 12/1989 | Poirier et al. |
| 4,892,518 A | 1/1990 | Cupp et al. |
| 4,895,561 A | 1/1990 | Mahurkar |
| 4,897,081 A | 1/1990 | Poirier et al. |
| 4,904,241 A | 2/1990 | Bark |
| 4,905,709 A | 3/1990 | Bieganski et al. |
| 4,908,029 A | 3/1990 | Bark et al. |
| 4,909,250 A | 3/1990 | Smith |
| 4,915,690 A | 4/1990 | Cone et al. |
| 4,928,298 A | 5/1990 | Tanaka |
| 4,929,236 A | 5/1990 | Sampson |
| 4,955,861 A | 9/1990 | Enegren et al. |
| 4,961,267 A | 10/1990 | Herzog |
| 4,963,133 A | 10/1990 | Whipple |
| 4,966,583 A | 10/1990 | Debbas |
| 4,973,319 A | 11/1990 | Melsky |
| 4,983,162 A | 1/1991 | Metais et al. |
| 5,002,735 A | 3/1991 | Alberhasky et al. |
| 5,006,115 A | 4/1991 | McDonald |
| 5,009,391 A | 4/1991 | Steigerwald |
| 5,009,644 A | 4/1991 | McDonald |
| 5,013,298 A | 5/1991 | Moden et al. |
| 5,041,098 A | 8/1991 | Loiterman et al. |
| 5,044,955 A | 9/1991 | Jagmin |
| 5,045,060 A | 9/1991 | Melsky et al. |
| 5,045,064 A | 9/1991 | Idriss |
| 5,053,013 A | 10/1991 | Ensminger et al. |
| 5,059,186 A | 10/1991 | Yamamoto et al. |
| 5,069,206 A | 12/1991 | Crosbie |

(56) References Cited

U.S. PATENT DOCUMENTS

| | | |
|---|---|---|
| 5,084,015 A | 1/1992 | Moriuchi |
| 5,085,216 A | 2/1992 | Henley, Jr. et al. |
| 5,090,066 A | 2/1992 | Schoepe et al. |
| 5,092,849 A | 3/1992 | Sampson |
| 5,108,317 A | 4/1992 | Beinhaur et al. |
| 5,108,375 A | 4/1992 | Harrison et al. |
| 5,108,377 A | 4/1992 | Cone et al. |
| 5,112,301 A | 5/1992 | Fenton, Jr. et al. |
| 5,112,303 A | 5/1992 | Pudenz et al. |
| 5,129,891 A | 7/1992 | Young |
| 5,137,529 A | 8/1992 | Watson et al. |
| 5,147,483 A | 9/1992 | Melsky et al. |
| 5,152,753 A | 10/1992 | Laguette et al. |
| 5,156,600 A | 10/1992 | Young |
| 5,158,547 A | 10/1992 | Doan et al. |
| 5,167,629 A | 12/1992 | Vertenstein et al. |
| 5,167,633 A | 12/1992 | Mann et al. |
| 5,167,638 A | 12/1992 | Felix et al. |
| 5,169,393 A | 12/1992 | Moorehead et al. |
| 5,171,228 A | 12/1992 | McDonald |
| 5,176,653 A | 1/1993 | Metals |
| 5,176,662 A | 1/1993 | Bartholomew et al. |
| 5,178,612 A | 1/1993 | Fenton, Jr. |
| 5,180,365 A | 1/1993 | Ensminger et al. |
| 5,185,003 A | 2/1993 | Brethauer |
| 5,189,690 A | 2/1993 | Samuel |
| 5,193,106 A | 3/1993 | DeSena |
| 5,195,122 A | 3/1993 | Fabian |
| 5,195,123 A | 3/1993 | Clement |
| 5,201,715 A | 4/1993 | Masters |
| 5,201,722 A | 4/1993 | Moorehead et al. |
| 5,203,771 A | 4/1993 | Melker et al. |
| 5,203,777 A | 4/1993 | Lee |
| 5,205,834 A | 4/1993 | Moorehead et al. |
| 5,207,644 A | 5/1993 | Strecker |
| 5,213,574 A | 5/1993 | Tucker |
| 5,215,537 A | 6/1993 | Lynn et al. |
| 5,222,499 A | 6/1993 | Allen et al. |
| D337,637 S | 7/1993 | Tucker |
| 5,224,938 A | 7/1993 | Fenton, Jr. |
| 5,242,415 A | 9/1993 | Kantrowitz et al. |
| 5,246,462 A | 9/1993 | Bekki et al. |
| 5,249,598 A | 10/1993 | Schmidt |
| 5,263,930 A | 11/1993 | Ensminger |
| D342,134 S | 12/1993 | Mongeon |
| 5,281,199 A | 1/1994 | Ensminger et al. |
| 5,281,205 A | 1/1994 | McPherson |
| 5,290,263 A | 3/1994 | Wigness et al. |
| 5,295,658 A | 3/1994 | Atkinson et al. |
| 5,299,253 A | 3/1994 | Wessels |
| 5,300,048 A | 4/1994 | Drewes, Jr. et al. |
| 5,309,863 A | 5/1994 | Leeb, Jr. |
| 5,312,337 A | 5/1994 | Flaherty et al. |
| 5,318,545 A | 6/1994 | Tucker |
| 5,320,100 A | 6/1994 | Herweck et al. |
| 5,328,480 A | 7/1994 | Melker et al. |
| 5,332,398 A | 7/1994 | Miller et al. |
| 5,336,194 A | 8/1994 | Polaschegg et al. |
| 5,338,398 A | 8/1994 | Szwejkowski et al. |
| 5,350,360 A | 9/1994 | Ensminger et al. |
| 5,352,204 A | 10/1994 | Ensminger |
| 5,356,381 A | 10/1994 | Ensminger et al. |
| 5,360,407 A | 11/1994 | Leonard et al. |
| 5,383,223 A | 1/1995 | Inokuchi |
| 5,383,233 A | 1/1995 | Russell |
| 5,383,585 A | 1/1995 | Weiss |
| 5,383,858 A | 1/1995 | Reilly et al. |
| D355,240 S | 2/1995 | Gladfelter et al. |
| 5,387,192 A | 2/1995 | Glantz et al. |
| 5,394,457 A | 2/1995 | Leibinger et al. |
| 5,395,324 A | 3/1995 | Hinrichs et al. |
| 5,396,925 A | 3/1995 | Poli |
| 5,397,329 A | 3/1995 | Allen |
| 5,399,168 A | 3/1995 | Wadsworth, Jr. et al. |
| 5,405,402 A | 4/1995 | Dye et al. |
| 5,417,565 A | 5/1995 | Long |
| 5,417,656 A | 5/1995 | Ensminger et al. |
| 5,421,814 A | 6/1995 | Geary |
| 5,423,334 A | 6/1995 | Jordan |
| 5,425,762 A | 6/1995 | Muller |
| 5,453,097 A | 9/1995 | Paradis |
| 5,456,698 A | 10/1995 | Byland et al. |
| 5,476,451 A | 12/1995 | Ensminger et al. |
| 5,476,460 A | 12/1995 | Montalvo |
| 5,476,880 A | 12/1995 | Cooke et al. |
| 5,484,402 A | 1/1996 | Saravia et al. |
| 5,503,630 A | 4/1996 | Ensminger et al. |
| 5,507,813 A | 4/1996 | Dowd et al. |
| 5,509,805 A | 4/1996 | Jagmin |
| 5,513,637 A | 5/1996 | Twiss et al. |
| 5,514,103 A | 5/1996 | Srisathapat et al. |
| 5,520,632 A | 5/1996 | Leveen et al. |
| 5,520,643 A | 5/1996 | Ensminger et al. |
| 5,527,277 A | 6/1996 | Ensminger et al. |
| 5,527,278 A | 6/1996 | Ensminger et al. |
| 5,527,307 A | 6/1996 | Srisathapat et al. |
| 5,531,684 A | 7/1996 | Ensminger et al. |
| 5,542,923 A | 8/1996 | Ensminger et al. |
| 5,545,143 A | 8/1996 | Fischell |
| 5,554,117 A | 9/1996 | Ensminger et al. |
| 5,556,381 A | 9/1996 | Ensminger et al. |
| 5,558,641 A | 9/1996 | Glantz et al. |
| 5,558,829 A | 9/1996 | Petrick |
| 5,562,617 A | 10/1996 | Finch, Jr. et al. |
| 5,562,618 A | 10/1996 | Cai et al. |
| 5,575,770 A | 11/1996 | Melsky et al. |
| 5,593,028 A | 1/1997 | Haber et al. |
| 5,593,434 A | 1/1997 | Williams |
| 5,607,393 A | 3/1997 | Ensminger et al. |
| 5,607,407 A | 3/1997 | Tolkoff et al. |
| 5,613,945 A | 3/1997 | Cai et al. |
| 5,620,419 A | 4/1997 | Lui et al. |
| 5,632,729 A | 5/1997 | Cai et al. |
| 5,637,102 A | 6/1997 | Tolkoff et al. |
| 5,638,832 A | 6/1997 | Singer et al. |
| 5,647,855 A | 7/1997 | Trooskin |
| RE35,601 E | 9/1997 | Eckenhoff |
| 5,662,600 A | 9/1997 | Watson et al. |
| 5,662,612 A | 9/1997 | Niehoff |
| 5,662,616 A | 9/1997 | Bousquet |
| 5,676,146 A | 10/1997 | Scarborough |
| 5,695,490 A | 12/1997 | Flaherty et al. |
| 5,702,128 A | 12/1997 | Maxim et al. |
| 5,702,363 A | 12/1997 | Flaherty |
| 5,704,915 A | 1/1998 | Melsky et al. |
| 5,707,357 A | 1/1998 | Mikhail et al. |
| 5,709,668 A | 1/1998 | Wacks |
| 5,713,844 A | 2/1998 | Peyman |
| 5,713,858 A | 2/1998 | Heruth et al. |
| 5,713,859 A | 2/1998 | Finch, Jr. et al. |
| 5,718,382 A | 2/1998 | Jaeger |
| 5,718,682 A | 2/1998 | Tucker |
| 5,725,507 A | 3/1998 | Petrick |
| 5,733,336 A | 3/1998 | Neuenfeldt et al. |
| 5,733,400 A | 3/1998 | Gore et al. |
| 5,741,228 A | 4/1998 | Lambrecht et al. |
| 5,743,873 A | 4/1998 | Cai et al. |
| 5,743,891 A | 4/1998 | Tolkoff et al. |
| 5,746,460 A | 5/1998 | Marohl et al. |
| 5,755,780 A | 5/1998 | Finch, Jr. et al. |
| 5,758,667 A | 6/1998 | Slettenmark |
| 5,769,823 A | 6/1998 | Otto |
| 5,773,552 A | 6/1998 | Hutchings et al. |
| 5,776,188 A | 7/1998 | Shepherd et al. |
| 5,792,104 A | 8/1998 | Speckman et al. |
| 5,792,116 A | 8/1998 | Berg et al. |
| 5,792,123 A | 8/1998 | Ensminger |
| 5,797,886 A | 8/1998 | Roth et al. |
| 5,810,789 A | 9/1998 | Powers et al. |
| 5,814,016 A | 9/1998 | Valley et al. |
| 5,824,071 A | 10/1998 | Nelson et al. |
| 5,830,172 A | 11/1998 | Leveen et al. |
| 5,833,654 A | 11/1998 | Powers et al. |
| 5,835,563 A | 11/1998 | Navab et al. |

(56) References Cited

U.S. PATENT DOCUMENTS

| | | |
|---|---|---|
| 5,836,935 A | 11/1998 | Ashton et al. |
| 5,840,063 A | 11/1998 | Flaherty |
| 5,843,069 A | 12/1998 | Butler et al. |
| 5,848,989 A | 12/1998 | Villani |
| 5,851,221 A | 12/1998 | Rieder et al. |
| 5,853,394 A | 12/1998 | Tolkoff et al. |
| 5,868,702 A | 2/1999 | Stevens et al. |
| 5,879,322 A | 3/1999 | Lattin et al. |
| 5,882,341 A | 3/1999 | Bousquet |
| 5,882,353 A | 3/1999 | VanBeek et al. |
| 5,895,424 A | 4/1999 | Steele, Sr. et al. |
| 5,897,528 A | 4/1999 | Schultz |
| 5,899,856 A | 5/1999 | Schoendorfer et al. |
| 5,904,934 A | 5/1999 | Maruyama et al. |
| 5,906,592 A | 5/1999 | Kriesel et al. |
| 5,906,596 A | 5/1999 | Tallarida |
| 5,908,413 A | 6/1999 | Lange et al. |
| 5,908,414 A | 6/1999 | Otto et al. |
| 5,911,706 A | 6/1999 | Estabrook et al. |
| 5,913,998 A | 6/1999 | Butler et al. |
| 5,916,263 A | 6/1999 | Goicoechea et al. |
| 5,919,160 A | 7/1999 | Sanfilippo, II |
| 5,925,017 A | 7/1999 | Kriesel et al. |
| 5,925,030 A | 7/1999 | Gross et al. |
| 5,927,345 A | 7/1999 | Samson |
| 5,928,197 A | 7/1999 | Niehoff |
| 5,928,744 A | 7/1999 | Heilmann et al. |
| 5,931,829 A | 8/1999 | Burbank et al. |
| 5,941,856 A | 8/1999 | Kovacs et al. |
| 5,944,023 A | 8/1999 | Johnson et al. |
| 5,944,688 A | 8/1999 | Lois |
| 5,944,698 A | 8/1999 | Fischer et al. |
| 5,944,712 A | 8/1999 | Frassica et al. |
| D413,672 S | 9/1999 | Fogarty |
| 5,947,953 A | 9/1999 | Ash et al. |
| 5,951,512 A | 9/1999 | Dalton |
| 5,951,522 A | 9/1999 | Rosato et al. |
| 5,951,929 A | 9/1999 | Wilson |
| 5,954,687 A | 9/1999 | Baudino |
| 5,954,691 A | 9/1999 | Prosl |
| 5,957,890 A | 9/1999 | Mann et al. |
| 5,961,497 A | 10/1999 | Larkin |
| 5,968,011 A | 10/1999 | Larsen et al. |
| 5,970,162 A | 10/1999 | Kawashima |
| 5,989,216 A | 11/1999 | Johnson et al. |
| 5,989,239 A | 11/1999 | Finch et al. |
| 5,989,641 A | 11/1999 | Oulie |
| 5,997,524 A | 12/1999 | Burbank et al. |
| 6,007,516 A | 12/1999 | Burbank et al. |
| 6,013,051 A | 1/2000 | Nelson |
| 6,013,058 A | 1/2000 | Prosl et al. |
| 6,017,331 A | 1/2000 | Walls et al. |
| 6,022,335 A | 2/2000 | Ramadan |
| 6,033,389 A | 3/2000 | Cornish |
| 6,039,712 A | 3/2000 | Fogarty et al. |
| 6,056,717 A | 5/2000 | Finch et al. |
| 6,077,756 A | 6/2000 | Lin et al. |
| 6,086,555 A | 7/2000 | Eliasen et al. |
| 6,090,066 A | 7/2000 | Schnell |
| 6,099,508 A | 8/2000 | Bousquet |
| 6,102,884 A | 8/2000 | Squitieri |
| 6,113,572 A | 9/2000 | Gailey et al. |
| 6,120,492 A | 9/2000 | Finch et al. |
| 6,152,909 A | 11/2000 | Bagaoisan et al. |
| 6,161,033 A | 12/2000 | Kuhn |
| 6,171,198 B1 | 1/2001 | Lizama Troncoso et al. |
| 6,171,298 B1 | 1/2001 | Matsuura et al. |
| 6,186,982 B1 | 2/2001 | Gross et al. |
| 6,190,352 B1 | 2/2001 | Haarala et al. |
| 6,193,684 B1 | 2/2001 | Burbank et al. |
| 6,198,807 B1 | 3/2001 | DeSena |
| 6,200,338 B1 | 3/2001 | Solomon et al. |
| 6,203,570 B1 | 3/2001 | Baeke |
| 6,210,366 B1 | 4/2001 | Sanfilippo, II |
| 6,213,973 B1 | 4/2001 | Eliasen et al. |
| 6,228,088 B1 | 5/2001 | Miller et al. |
| 6,251,059 B1 | 6/2001 | Apple et al. |
| D445,175 S | 7/2001 | Bertheas |
| 6,261,259 B1 | 7/2001 | Bell |
| 6,269,148 B1 | 7/2001 | Jessop et al. |
| 6,272,370 B1 | 8/2001 | Gillies et al. |
| 6,287,293 B1 | 9/2001 | Jones et al. |
| 6,290,677 B1 | 9/2001 | Arai et al. |
| 6,305,413 B1 | 10/2001 | Fischer et al. |
| 6,306,124 B1 | 10/2001 | Jones et al. |
| D450,115 S | 11/2001 | Bertheas |
| 6,315,762 B1 | 11/2001 | Recinella et al. |
| 6,332,874 B1 | 12/2001 | Eliasen et al. |
| 6,351,513 B1 | 2/2002 | Bani-Hashemi et al. |
| 6,355,021 B1 | 3/2002 | Nielsen et al. |
| 6,356,782 B1 | 3/2002 | Sirimanne et al. |
| 6,361,557 B1 | 3/2002 | Gittings et al. |
| 6,398,764 B1 | 6/2002 | Finch, Jr. et al. |
| 6,419,680 B1 | 7/2002 | Cosman et al. |
| 6,450,937 B1 | 9/2002 | Mercereau et al. |
| 6,459,772 B1 | 10/2002 | Wiedenhoefer et al. |
| 6,473,638 B2 | 10/2002 | Ferek-Petric |
| 6,475,516 B2 | 11/2002 | DiCosmo et al. |
| 6,478,783 B1 | 11/2002 | Moorehead |
| 6,482,217 B1 | 11/2002 | Pintor et al. |
| 6,494,867 B1 | 12/2002 | Elver et al. |
| 6,497,062 B1 | 12/2002 | Koopman et al. |
| 6,500,155 B2 | 12/2002 | Sasso |
| 6,503,228 B1 | 1/2003 | Li et al. |
| 6,527,754 B1 | 3/2003 | Tallarida et al. |
| 6,537,255 B1 | 3/2003 | Raines |
| RE38,074 E | 4/2003 | Recinella et al. |
| 6,562,023 B1 | 5/2003 | Marrs et al. |
| 6,572,583 B1 | 6/2003 | Olsen et al. |
| 6,582,418 B1 | 6/2003 | Verbeek et al. |
| 6,592,571 B1 | 7/2003 | Verbeek et al. |
| 6,610,031 B1 | 8/2003 | Chin |
| 6,613,002 B1 | 9/2003 | Clark et al. |
| 6,613,662 B2 | 9/2003 | Wark et al. |
| 6,626,936 B2 | 9/2003 | Stinson |
| D480,942 S | 10/2003 | Ishida et al. |
| 6,629,950 B1 | 10/2003 | Levin |
| 6,632,217 B2 | 10/2003 | Harper et al. |
| 6,652,486 B2 | 11/2003 | Bialecki et al. |
| 6,652,503 B1 | 11/2003 | Bradley |
| 6,663,646 B1 | 12/2003 | Shah |
| 6,676,633 B2 | 1/2004 | Smith et al. |
| 6,697,664 B2 | 2/2004 | Kienzle, III et al. |
| 6,705,316 B2 | 3/2004 | Blythe et al. |
| 6,719,721 B1 | 4/2004 | Okazaki et al. |
| 6,719,739 B2 | 4/2004 | Verbeek et al. |
| 6,726,063 B2 | 4/2004 | Stull et al. |
| 6,738,531 B1 | 5/2004 | Funahashi |
| 6,755,842 B2 | 6/2004 | Kanner et al. |
| 6,758,841 B2 | 7/2004 | Haarala et al. |
| 6,767,356 B2 | 7/2004 | Kanner et al. |
| 6,784,783 B2 | 8/2004 | Scoggin et al. |
| 6,808,738 B2 | 10/2004 | DiTizio et al. |
| D498,894 S | 11/2004 | Gould |
| 6,826,257 B2 | 11/2004 | Sayre et al. |
| 6,827,709 B2 | 12/2004 | Fujii |
| 6,852,106 B2 | 2/2005 | Watson et al. |
| 6,856,055 B2 | 2/2005 | Michaels et al. |
| 6,878,136 B2 | 4/2005 | Fleury et al. |
| 6,878,137 B2 | 4/2005 | Benchetrit |
| 6,929,631 B1 | 8/2005 | Brugger et al. |
| 6,949,084 B2 | 9/2005 | Marggi et al. |
| 6,953,453 B2 | 10/2005 | Recinella et al. |
| 6,962,577 B2 | 11/2005 | Tallarida et al. |
| 6,962,580 B2 | 11/2005 | Adams et al. |
| 6,994,315 B2 | 2/2006 | Ryan et al. |
| 6,997,914 B2 | 2/2006 | Smith et al. |
| 7,008,377 B2 | 3/2006 | Beane et al. |
| 7,008,412 B2 | 3/2006 | Maginot |
| 7,016,456 B2 | 3/2006 | Basu et al. |
| 7,018,361 B2 | 3/2006 | Gillespie, Jr. et al. |
| D518,573 S | 4/2006 | French |
| 7,033,335 B2 | 4/2006 | Haarala et al. |
| 7,033,339 B1 | 4/2006 | Lynn |

(56) References Cited

U.S. PATENT DOCUMENTS

| | | |
|---|---|---|
| 7,044,942 B2 | 5/2006 | Jolly et al. |
| 7,056,316 B1 | 6/2006 | Burbank et al. |
| 7,070,591 B2 | 7/2006 | Adams et al. |
| 7,072,704 B2 | 7/2006 | Bucholz |
| 7,074,232 B2 | 7/2006 | Kanner et al. |
| 7,076,305 B2 | 7/2006 | Imran et al. |
| 7,083,593 B2 | 8/2006 | Stultz |
| 7,108,686 B2 | 9/2006 | Burke et al. |
| 7,123,690 B1 | 10/2006 | Brown et al. |
| 7,124,570 B2 | 10/2006 | Blatter et al. |
| 7,127,040 B2 | 10/2006 | Sayre et al. |
| 7,131,962 B1 | 11/2006 | Estabrook et al. |
| 7,140,769 B2 | 11/2006 | Kay |
| 7,186,236 B2 | 3/2007 | Gibson et al. |
| 7,191,011 B2 | 3/2007 | Cantlon |
| 7,198,631 B2 | 4/2007 | Kanner et al. |
| 7,214,207 B2 | 5/2007 | Lynch et al. |
| 7,214,215 B2 | 5/2007 | Heinzerling et al. |
| 7,223,257 B2 | 5/2007 | Shubayev et al. |
| 7,229,417 B2 | 6/2007 | Foerster et al. |
| 7,232,429 B2 | 6/2007 | Moreci |
| 7,235,067 B2 | 6/2007 | Morris et al. |
| D546,440 S | 7/2007 | Burnside |
| 7,242,982 B2 | 7/2007 | Singhal et al. |
| 7,248,668 B2 | 7/2007 | Galkin |
| 7,252,469 B2 | 8/2007 | Zaluzec et al. |
| 7,252,649 B2 | 8/2007 | Sherry |
| 7,261,705 B2 | 8/2007 | Edoga et al. |
| D550,355 S | 9/2007 | Racz et al. |
| D554,253 S | 10/2007 | Komerup |
| 7,275,682 B2 | 10/2007 | Excoffier et al. |
| 7,276,075 B1 | 10/2007 | Callas et al. |
| D556,153 S | 11/2007 | Burnside |
| 7,306,579 B2 | 12/2007 | Fujii |
| 7,311,702 B2 | 12/2007 | Tallarida et al. |
| 7,318,816 B2 | 1/2008 | Bobroff et al. |
| 7,318,818 B2 | 1/2008 | Yashiro et al. |
| 7,322,953 B2 | 1/2008 | Redinger |
| D562,442 S | 2/2008 | Blateri |
| D562,443 S | 2/2008 | Zinn et al. |
| 7,331,130 B2 | 2/2008 | Schweikert |
| 7,331,948 B2 | 2/2008 | Skarda |
| 7,333,013 B2 | 2/2008 | Berger |
| D564,449 S | 3/2008 | Dewberry |
| 7,347,838 B2 | 3/2008 | Kulli |
| 7,347,843 B2 | 3/2008 | Adams et al. |
| 7,351,233 B2 | 4/2008 | Parks |
| 7,377,915 B2 | 5/2008 | Rasmussen et al. |
| D574,950 S | 8/2008 | Zawacki et al. |
| 7,413,564 B2 | 8/2008 | Morris et al. |
| D578,203 S | 10/2008 | Bizup |
| 7,445,614 B2 | 11/2008 | Bunodiere et al. |
| D582,032 S | 12/2008 | Bizup et al. |
| 7,465,847 B2 | 12/2008 | Fabian |
| 7,485,148 B2 | 2/2009 | Wozencroft et al. |
| 7,497,850 B2 | 3/2009 | Halili |
| D590,499 S | 4/2009 | Chesnin |
| 7,552,853 B2 | 6/2009 | Mas et al. |
| 7,553,298 B2 | 6/2009 | Hunt et al. |
| D595,892 S | 7/2009 | Smith et al. |
| 7,563,025 B2 | 7/2009 | Kay |
| 7,618,411 B2 | 11/2009 | Appling |
| 7,628,776 B2 | 12/2009 | Gibson et al. |
| 7,658,196 B2 | 2/2010 | Ferreri et al. |
| D612,479 S | 3/2010 | Lawacki et al. |
| D613,394 S | 4/2010 | Linden |
| 7,713,251 B2 | 5/2010 | Tallarida et al. |
| 7,722,580 B2 | 5/2010 | Dicarlo et al. |
| D619,242 S | 7/2010 | Zinn et al. |
| 7,766,880 B1 | 8/2010 | Spinoza |
| 7,785,302 B2 | 8/2010 | Powers |
| 7,803,143 B2 | 9/2010 | Tallarida et al. |
| 7,806,888 B2 | 10/2010 | Frassica |
| 7,811,266 B2 | 10/2010 | Eliasen |
| D629,503 S | 12/2010 | Caffey et al. |
| 7,846,139 B2 | 12/2010 | Zinn et al. |
| 7,850,660 B2 | 12/2010 | Uth et al. |
| 7,862,546 B2 | 1/2011 | Conlon et al. |
| D634,840 S | 3/2011 | Lombardi, III et al. |
| 7,909,804 B2 | 3/2011 | Stats |
| 7,931,619 B2 | 4/2011 | Diamond et al. |
| 7,947,022 B2 | 5/2011 | Amin et al. |
| 7,959,615 B2 | 6/2011 | Stats et al. |
| 7,972,314 B2 | 7/2011 | Bizup et al. |
| 8,007,474 B2 | 8/2011 | Uth et al. |
| 8,021,324 B2 | 9/2011 | Bizup et al. |
| 8,025,639 B2 | 9/2011 | Powers et al. |
| 8,029,482 B2 | 10/2011 | Maniar et al. |
| D650,475 S | 12/2011 | Smith et al. |
| 8,075,536 B2 | 12/2011 | Gray et al. |
| 8,092,435 B2 | 1/2012 | Beling et al. |
| 8,147,455 B2 | 4/2012 | Butts et al. |
| 8,172,894 B2 | 5/2012 | Schmid et al. |
| 8,172,896 B2 | 5/2012 | McNamara et al. |
| 8,177,762 B2 | 5/2012 | Beasley et al. |
| 8,182,453 B2 | 5/2012 | Eliasen |
| 8,197,454 B2 | 6/2012 | Mann et al. |
| 8,202,259 B2 | 6/2012 | Evans et al. |
| 8,257,325 B2 | 9/2012 | Schweikert et al. |
| D676,955 S | 2/2013 | Orome |
| 8,366,687 B2 | 2/2013 | Girard et al. |
| 8,377,034 B2 | 2/2013 | Tallarida et al. |
| 8,382,723 B2 | 2/2013 | Powers et al. |
| 8,382,724 B2 | 2/2013 | Maniar et al. |
| 8,409,153 B2 | 4/2013 | Tallarida et al. |
| 8,475,417 B2 | 7/2013 | Powers et al. |
| 8,545,460 B2 | 10/2013 | Beasley et al. |
| 8,585,660 B2 | 11/2013 | Murphy |
| 8,585,663 B2 | 11/2013 | Powers et al. |
| 8,603,052 B2 | 12/2013 | Powers et al. |
| 8,608,712 B2 | 12/2013 | Bizup et al. |
| 8,608,713 B2 | 12/2013 | Beasley et al. |
| 8,641,676 B2 | 2/2014 | Butts et al. |
| 8,641,688 B2 | 2/2014 | Powers et al. |
| 8,805,478 B2 | 8/2014 | Powers et al. |
| 8,852,160 B2 | 10/2014 | Schweikert et al. |
| 8,932,271 B2 | 1/2015 | Hamatake et al. |
| 8,939,947 B2 | 1/2015 | Maniar et al. |
| 8,998,860 B2 | 4/2015 | Sheetz et al. |
| 9,079,004 B2 | 7/2015 | Wiley et al. |
| 9,248,268 B2 | 2/2016 | Wiley et al. |
| 9,265,912 B2 | 2/2016 | Draper et al. |
| 9,295,733 B2 | 3/2016 | Trieu |
| 9,421,352 B2 | 8/2016 | Butts et al. |
| 9,579,496 B2 | 2/2017 | Evans et al. |
| 9,603,992 B2 | 3/2017 | Powers |
| 9,603,993 B2 | 3/2017 | Powers |
| 10,052,470 B2 | 8/2018 | Powers et al. |
| 10,052,471 B2 | 8/2018 | Hamatake et al. |
| 2001/0016699 A1 | 8/2001 | Burbank et al. |
| 2001/0016717 A1 | 8/2001 | Haarala et al. |
| 2001/0047165 A1 | 11/2001 | Makower et al. |
| 2001/0051766 A1 | 12/2001 | Gazdzinski |
| 2001/0053889 A1 | 12/2001 | Marggi et al. |
| 2001/0056266 A1 | 12/2001 | Tallarida et al. |
| 2002/0013557 A1 | 1/2002 | Sherry |
| 2002/0052576 A1 | 5/2002 | Massengale |
| 2002/0055715 A1 | 5/2002 | Young et al. |
| 2002/0095205 A1 | 7/2002 | Edwin et al. |
| 2002/0121530 A1 | 9/2002 | Socier |
| 2002/0138068 A1 | 9/2002 | Watson et al. |
| 2002/0169418 A1 | 11/2002 | Menzi et al. |
| 2002/0173769 A1 | 11/2002 | Gray et al. |
| 2002/0173772 A1 | 11/2002 | Olsen |
| 2002/0183846 A1 | 12/2002 | Kuslich et al. |
| 2002/0188282 A1 | 12/2002 | Greenberg |
| 2003/0028173 A1 | 2/2003 | Forsberg |
| 2003/0093029 A1 | 5/2003 | McGuckin et al. |
| 2003/0109856 A1 | 6/2003 | Sherry |
| 2003/0130627 A1 | 7/2003 | Smith et al. |
| 2003/0135388 A1 | 7/2003 | Martucci et al. |
| 2003/0139812 A1 | 7/2003 | Garcia et al. |
| 2003/0141477 A1 | 7/2003 | Miller |
| 2003/0181878 A1 | 9/2003 | Tallarida et al. |

(56) References Cited

U.S. PATENT DOCUMENTS

| | | |
|---|---|---|
| 2003/0191452 A1 | 10/2003 | Meglin et al. |
| 2003/0208184 A1 | 11/2003 | Burke et al. |
| 2003/0216694 A1 | 11/2003 | Tollini |
| 2003/0217659 A1 | 11/2003 | Yamamoto et al. |
| 2004/0002693 A1 | 1/2004 | Bright et al. |
| 2004/0006316 A1 | 1/2004 | Patton |
| 2004/0020462 A1 | 2/2004 | Sauler et al. |
| 2004/0020492 A1 | 2/2004 | Dubrul et al. |
| 2004/0024361 A1 | 2/2004 | Fago et al. |
| 2004/0044306 A1 | 3/2004 | Lynch et al. |
| 2004/0054352 A1 | 3/2004 | Adams et al. |
| 2004/0056266 A1 | 3/2004 | Suh et al. |
| 2004/0064110 A1 | 4/2004 | Forsell |
| 2004/0073196 A1 | 4/2004 | Adams et al. |
| 2004/0078000 A1 | 4/2004 | Borchard et al. |
| 2004/0086568 A1 | 5/2004 | Ditizio et al. |
| 2004/0087877 A1 | 5/2004 | Besz et al. |
| 2004/0087885 A1 | 5/2004 | Kawano et al. |
| 2004/0106878 A1 | 6/2004 | Skujins et al. |
| 2004/0106891 A1 | 6/2004 | Langan et al. |
| 2004/0106942 A1 | 6/2004 | Taylor et al. |
| 2004/0116901 A1 | 6/2004 | Appling |
| 2004/0133173 A1 | 7/2004 | Edoga et al. |
| 2004/0156472 A1 | 8/2004 | Galkin |
| 2004/0157952 A1 | 8/2004 | Soffiati et al. |
| 2004/0158207 A1 | 8/2004 | Hunn et al. |
| 2004/0167543 A1 | 8/2004 | Mazzocchi et al. |
| 2004/0176743 A1 | 9/2004 | Morris et al. |
| 2004/0186444 A1 | 9/2004 | Daly et al. |
| 2004/0199129 A1 | 10/2004 | DiMatteo |
| 2004/0199220 A1 | 10/2004 | Cantlon |
| 2004/0204692 A1 | 10/2004 | Eliasen |
| 2004/0204759 A1 | 10/2004 | Blom et al. |
| 2004/0225254 A1 | 11/2004 | Tanaka et al. |
| 2004/0254536 A1 | 12/2004 | Conlon et al. |
| 2004/0254537 A1 | 12/2004 | Conlon et al. |
| 2005/0010176 A1 | 1/2005 | Dikeman et al. |
| 2005/0010286 A1 | 1/2005 | Vijay |
| 2005/0027234 A1 | 2/2005 | Waggoner et al. |
| 2005/0027261 A1 | 2/2005 | Weaver et al. |
| 2005/0038390 A1 | 2/2005 | Fago |
| 2005/0044759 A1 | 3/2005 | Schweikert |
| 2005/0049553 A1 | 3/2005 | Triplett et al. |
| 2005/0070875 A1 | 3/2005 | Kulessa |
| 2005/0075614 A1 | 4/2005 | Bunodiere et al. |
| 2005/0080401 A1 | 4/2005 | Peavey |
| 2005/0085778 A1 | 4/2005 | Parks |
| 2005/0086071 A1 | 4/2005 | Fox et al. |
| 2005/0113806 A1 | 5/2005 | De Carvalho et al. |
| 2005/0124980 A1 | 6/2005 | Sanders |
| 2005/0131352 A1 | 6/2005 | Conlon et al. |
| 2005/0148866 A1 | 7/2005 | Gunderson |
| 2005/0148869 A1 | 7/2005 | Masuda |
| 2005/0148956 A1 | 7/2005 | Conlon et al. |
| 2005/0148957 A1 | 7/2005 | Girard et al. |
| 2005/0152841 A1 | 7/2005 | Sayre et al. |
| 2005/0171502 A1 | 8/2005 | Daly et al. |
| 2005/0182857 A1 | 8/2005 | Kong |
| 2005/0209573 A1 | 9/2005 | Brugger et al. |
| 2005/0215874 A1 | 9/2005 | Wang et al. |
| 2005/0241203 A1 | 11/2005 | Lizotte et al. |
| 2005/0256451 A1 | 11/2005 | Adams et al. |
| 2005/0256500 A1 | 11/2005 | Fujii |
| 2005/0277899 A1 | 12/2005 | Conlon et al. |
| 2005/0283119 A1 | 12/2005 | Uth et al. |
| 2006/0009788 A1 | 1/2006 | Freeman et al. |
| 2006/0017341 A1 | 1/2006 | Hahn et al. |
| 2006/0020256 A1 | 1/2006 | Bell et al. |
| 2006/0084929 A1 | 4/2006 | Eliasen |
| 2006/0089619 A1 | 4/2006 | Ginggen |
| 2006/0100592 A1 | 5/2006 | Eliasen |
| 2006/0116648 A1 | 6/2006 | Hamatake |
| 2006/0149189 A1 | 7/2006 | Diamond et al. |
| 2006/0171980 A1 | 8/2006 | Helmus et al. |
| 2006/0173410 A1 | 8/2006 | Moberg et al. |
| 2006/0173424 A1 | 8/2006 | Conlon |
| 2006/0178647 A1 | 8/2006 | Stats |
| 2006/0178648 A1 | 8/2006 | Barron et al. |
| 2006/0184141 A1 | 8/2006 | Smith et al. |
| 2006/0184142 A1 | 8/2006 | Schon et al. |
| 2006/0217359 A1 | 9/2006 | Wentworth et al. |
| 2006/0217659 A1 | 9/2006 | Patton |
| 2006/0217668 A1 | 9/2006 | Schulze et al. |
| 2006/0224128 A1 | 10/2006 | Lurvey et al. |
| 2006/0224129 A1 | 10/2006 | Beasley et al. |
| 2006/0224235 A1 | 10/2006 | Rucker |
| 2006/0241465 A1 | 10/2006 | Huennekens et al. |
| 2006/0247584 A1 | 11/2006 | Sheetz et al. |
| 2006/0253076 A1 | 11/2006 | Butts et al. |
| 2006/0264897 A1 | 11/2006 | Lobl et al. |
| 2006/0264898 A1 | 11/2006 | Beasley et al. |
| 2006/0271012 A1 | 11/2006 | Canaud et al. |
| 2007/0003603 A1 | 1/2007 | Karandikar et al. |
| 2007/0004981 A1 | 1/2007 | Boese et al. |
| 2007/0007839 A1 | 1/2007 | Lin |
| 2007/0010881 A1 | 1/2007 | Soye et al. |
| 2007/0016162 A1 | 1/2007 | Burbank et al. |
| 2007/0049806 A1 | 3/2007 | Adams et al. |
| 2007/0049876 A1 | 3/2007 | Patton |
| 2007/0055290 A1 | 3/2007 | Lober |
| 2007/0073250 A1 | 3/2007 | Schneiter |
| 2007/0078391 A1 | 4/2007 | Wortley et al. |
| 2007/0078416 A1 | 4/2007 | Eliasen |
| 2007/0078432 A1 | 4/2007 | Halseth et al. |
| 2007/0083111 A1 | 4/2007 | Hossack et al. |
| 2007/0083156 A1 | 4/2007 | Muto et al. |
| 2007/0100302 A1 | 5/2007 | Dicarlo et al. |
| 2007/0112332 A1 | 5/2007 | Harding et al. |
| 2007/0120683 A1 | 5/2007 | Flippen et al. |
| 2007/0123831 A1 | 5/2007 | Haindl et al. |
| 2007/0135775 A1 | 6/2007 | Edoga et al. |
| 2007/0149920 A1 | 6/2007 | Michels et al. |
| 2007/0149921 A1 | 6/2007 | Michels et al. |
| 2007/0149947 A1 | 6/2007 | Byrum |
| 2007/0161958 A1 | 7/2007 | Glenn |
| 2007/0179456 A1 | 8/2007 | Glenn |
| 2007/0185462 A1 | 8/2007 | Byrum |
| 2007/0191773 A1 | 8/2007 | Wojcik |
| 2007/0207335 A1 | 9/2007 | Karandikar et al. |
| 2007/0208313 A1 | 9/2007 | Conlon et al. |
| 2007/0219510 A1 | 9/2007 | Zinn et al. |
| 2007/0233017 A1 | 10/2007 | Zinn et al. |
| 2007/0233018 A1 | 10/2007 | Bizup et al. |
| 2007/0233042 A1 | 10/2007 | Moehle et al. |
| 2007/0255226 A1 | 11/2007 | Tennican et al. |
| 2007/0255234 A1 | 11/2007 | Haase et al. |
| 2007/0270691 A1 | 11/2007 | Bailey et al. |
| 2007/0270770 A1 | 11/2007 | Bizup |
| 2007/0276344 A1 | 11/2007 | Bizup et al. |
| 2007/0276355 A1 | 11/2007 | Nielsen et al. |
| 2007/0282308 A1 | 12/2007 | Bell |
| 2007/0293800 A1 | 12/2007 | McMaken et al. |
| 2007/0299408 A1 | 12/2007 | Alferness et al. |
| 2008/0004642 A1 | 1/2008 | Birk et al. |
| 2008/0008654 A1 | 1/2008 | Clarke et al. |
| 2008/0015701 A1 | 1/2008 | Garcia et al. |
| 2008/0021392 A1 | 1/2008 | Lurvey et al. |
| 2008/0039820 A1 | 2/2008 | Sommers et al. |
| 2008/0048855 A1 | 2/2008 | Berger |
| 2008/0051731 A1 | 2/2008 | Schweikert et al. |
| 2008/0108949 A1 | 5/2008 | Beasley et al. |
| 2008/0114308 A1 | 5/2008 | di Palma et al. |
| 2008/0133265 A1 | 6/2008 | Silkaitis et al. |
| 2008/0137923 A1 | 6/2008 | Spahn |
| 2008/0138387 A1 | 6/2008 | Machiraju |
| 2008/0208236 A1 | 8/2008 | Hobbs et al. |
| 2008/0281279 A1 | 11/2008 | Hoendervoogt et al. |
| 2008/0319398 A1 | 12/2008 | Bizup |
| 2008/0319399 A1 | 12/2008 | Schweikert et al. |
| 2008/0319405 A1 | 12/2008 | Bizup |
| 2009/0024024 A1 | 1/2009 | Zinn |
| 2009/0024098 A1 | 1/2009 | Bizup et al. |
| 2009/0035582 A1 | 2/2009 | Nakatani et al. |
| 2009/0118683 A1 | 5/2009 | Hanson et al. |

(56) References Cited

U.S. PATENT DOCUMENTS

| | | |
|---|---|---|
| 2009/0156928 A1 | 6/2009 | Evans et al. |
| 2009/0204072 A1 | 8/2009 | Amin et al. |
| 2009/0204074 A1 | 8/2009 | Powers et al. |
| 2009/0216216 A1 | 8/2009 | Powers et al. |
| 2009/0221976 A1 | 9/2009 | Linden |
| 2009/0227862 A1 | 9/2009 | Smith et al. |
| 2009/0227951 A1 | 9/2009 | Powers et al. |
| 2009/0227964 A1 | 9/2009 | DiCarlo et al. |
| 2009/0264901 A1 | 10/2009 | Franklin et al. |
| 2009/0315684 A1 | 12/2009 | Sacco et al. |
| 2009/0322541 A1 | 12/2009 | Jones et al. |
| 2010/0010339 A1 | 1/2010 | Smith et al. |
| 2010/0042073 A1 | 2/2010 | Oster et al. |
| 2010/0063451 A1 | 3/2010 | Gray et al. |
| 2010/0069743 A1 | 3/2010 | Sheetz et al. |
| 2010/0106094 A1 | 4/2010 | Fisher et al. |
| 2010/0121283 A1 | 5/2010 | Hamatake et al. |
| 2010/0211026 A2 | 8/2010 | Sheetz et al. |
| 2010/0268165 A1 | 10/2010 | Maniar et al. |
| 2010/0268174 A1 | 10/2010 | Steinke et al. |
| 2010/0319700 A1 | 12/2010 | Ng et al. |
| 2011/0021922 A1 | 1/2011 | Berard-Anderson et al. |
| 2011/0092921 A1 | 4/2011 | Beling et al. |
| 2011/0098662 A1 | 4/2011 | Zinn |
| 2011/0098663 A1 | 4/2011 | Zinn |
| 2011/0118677 A1 | 5/2011 | Wiley et al. |
| 2011/0160673 A1 | 6/2011 | Magalich et al. |
| 2011/0183712 A1 | 7/2011 | Eckstein et al. |
| 2011/0213700 A1 | 9/2011 | Sant'Anselmo |
| 2011/0257609 A1 | 10/2011 | Bizup et al. |
| 2011/0264058 A1 | 10/2011 | Linden et al. |
| 2011/0271856 A1 | 11/2011 | Fisher et al. |
| 2011/0275930 A1 | 11/2011 | Jho et al. |
| 2011/0276015 A1 | 11/2011 | Powers et al. |
| 2011/0288502 A1 | 11/2011 | Hibdon et al. |
| 2011/0288503 A1 | 11/2011 | Magalich et al. |
| 2011/0311337 A1 | 12/2011 | Amin et al. |
| 2012/0018073 A1 | 1/2012 | Maniar et al. |
| 2012/0059250 A1 | 3/2012 | Gray et al. |
| 2012/0065622 A1 | 3/2012 | Cornish et al. |
| 2012/0078201 A1 | 3/2012 | Mikami |
| 2012/0078202 A1 | 3/2012 | Beling et al. |
| 2012/0191071 A1 | 7/2012 | Butts et al. |
| 2012/0226244 A1 | 9/2012 | Beasley et al. |
| 2012/0259296 A1 | 10/2012 | Sheetz et al. |
| 2012/0283560 A1 | 11/2012 | Schweikert et al. |
| 2012/0302969 A1 | 11/2012 | Wiley et al. |
| 2013/0165773 A1 | 6/2013 | Powers et al. |
| 2013/0172733 A1 | 7/2013 | Maniar et al. |
| 2013/0218103 A1 | 8/2013 | Tallarida et al. |
| 2013/0225990 A1 | 8/2013 | Powers et al. |
| 2013/0225991 A1 | 8/2013 | Powers |
| 2013/0245574 A1 | 9/2013 | Powers et al. |
| 2013/0338494 A1 | 12/2013 | Wiley et al. |
| 2014/0058275 A1 | 2/2014 | Gregorich et al. |
| 2014/0081219 A1 | 3/2014 | Powers et al. |
| 2014/0100534 A1 | 4/2014 | Beasley et al. |
| 2014/0107619 A1 | 4/2014 | Butts et al. |
| 2014/0330118 A1 | 11/2014 | Powers et al. |
| 2015/0008891 A1 | 1/2015 | Li et al. |
| 2015/0025478 A1 | 1/2015 | Hibdon et al. |
| 2015/0088091 A1 | 3/2015 | Beasley et al. |
| 2015/0112284 A1 | 4/2015 | Hamatake et al. |
| 2015/0290445 A1 | 10/2015 | Powers et al. |
| 2015/0290446 A1 | 10/2015 | Wiley et al. |
| 2017/0028185 A1 | 2/2017 | Wiley et al. |

FOREIGN PATENT DOCUMENTS

| | | |
|---|---|---|
| CA | 2692142 A1 | 12/2008 |
| CA | 2693972 A1 | 1/2009 |
| CN | 102421469 A | 4/2012 |
| CN | 102612343 A | 7/2012 |
| DE | 3618390 C1 | 11/1987 |
| DE | 3720414 A1 | 12/1987 |
| DE | 42 25 524 A1 | 2/1994 |
| DE | 29512576 U1 | 10/1995 |
| DE | 10346470 A1 | 5/2005 |
| DE | 10 2009 018837 A1 | 11/2010 |
| EP | 0128525 A2 | 12/1984 |
| EP | 0134745 A1 | 3/1985 |
| EP | 0343910 A2 | 11/1989 |
| EP | 0366814 A1 | 5/1990 |
| EP | 0239244 | 9/1991 |
| EP | 0534782 A1 | 3/1993 |
| EP | 0537892 A1 | 4/1993 |
| EP | 0619101 A1 | 10/1994 |
| EP | 1238682 A2 | 9/2002 |
| EP | 1486229 A1 | 12/2004 |
| EP | 1635899 A2 | 3/2006 |
| EP | 1858565 A1 | 11/2007 |
| EP | 1874393 A1 | 1/2008 |
| EP | 1896117 A2 | 3/2008 |
| EP | 1998842 A2 | 12/2008 |
| EP | 2004272 A2 | 12/2008 |
| EP | 2018209 A2 | 1/2009 |
| EP | 2081634 A1 | 7/2009 |
| EP | 2164559 A1 | 3/2010 |
| EP | 2167182 A1 | 3/2010 |
| EP | 2180915 A1 | 5/2010 |
| EP | 2190517 A1 | 6/2010 |
| EP | 2320974 A1 | 5/2011 |
| EP | 2324879 A2 | 5/2011 |
| EP | 2365838 A1 | 9/2011 |
| EP | 2571563 A1 | 3/2013 |
| EP | 2601999 A1 | 6/2013 |
| EP | 2324879 B1 | 1/2014 |
| EP | 2324878 B1 | 8/2014 |
| EP | 2308547 B1 | 9/2014 |
| EP | 2324880 B1 | 12/2014 |
| EP | 1 965 854 B1 | 9/2015 |
| EP | 2939703 B1 | 3/2017 |
| FR | 1509165 A | 1/1968 |
| FR | 2508008 A | 12/1982 |
| FR | 2809315 A1 | 11/2001 |
| GB | 178998 A | 5/1922 |
| GB | 749942 A | 6/1956 |
| GB | 966137 A | 8/1964 |
| GB | 1559140 A | 1/1980 |
| GB | 2102398 A | 2/1983 |
| GB | 2191701 A | 12/1987 |
| GB | 2350352 A | 11/2000 |
| JP | 62155857 A | 7/1987 |
| JP | 62281966 A | 12/1987 |
| JP | 64-011562 | 1/1989 |
| JP | H05-200107 A | 8/1993 |
| JP | 6296633 A | 10/1994 |
| JP | 2000-79168 | 3/2000 |
| JP | 2000-079168 A | 3/2000 |
| JP | 2002500076 A | 1/2002 |
| JP | 2002-83281 A | 3/2002 |
| JP | 2002-209910 A | 7/2002 |
| JP | 2002-531149 A | 9/2002 |
| JP | 2003-510136 A | 3/2003 |
| JP | 2004-350937 A | 12/2004 |
| JP | 2006025948 A | 2/2006 |
| JP | 2007-533368 A | 11/2007 |
| JP | 3142990 U | 7/2008 |
| JP | 2008-539025 A | 11/2008 |
| JP | 2009-077965 A | 4/2009 |
| JP | 2009-142520 A | 7/2009 |
| JP | 2012-523284 A | 10/2012 |
| JP | 2013-510652 | 3/2013 |
| JP | 2013-526376 A | 6/2013 |
| WO | 8600213 A1 | 1/1986 |
| WO | 1986000213 A1 | 1/1986 |
| WO | 1989011309 A1 | 11/1989 |
| WO | 9001958 A1 | 3/1990 |
| WO | 1990001958 A1 | 3/1990 |
| WO | 9206732 A1 | 4/1992 |
| WO | 1993000945 A1 | 1/1993 |
| WO | 9305730 A1 | 4/1993 |
| WO | 1993005730 A1 | 4/1993 |
| WO | 1993008986 A1 | 5/1993 |

(56) References Cited

FOREIGN PATENT DOCUMENTS

| | | |
|---|---|---|
| WO | 9405351 A1 | 3/1994 |
| WO | 9516480 A1 | 6/1995 |
| WO | 1995015194 | 6/1995 |
| WO | 96-35477 A1 | 11/1996 |
| WO | 9701370 A1 | 1/1997 |
| WO | 1997001370 A1 | 1/1997 |
| WO | 1997006845 A1 | 2/1997 |
| WO | 9711726 A1 | 4/1997 |
| WO | 9723255 A1 | 7/1997 |
| WO | 9726931 A1 | 7/1997 |
| WO | 1998017337 A1 | 4/1998 |
| WO | 9818506 A1 | 5/1998 |
| WO | 1998031417 A2 | 7/1998 |
| WO | 99/10250 A1 | 3/1999 |
| WO | 1999034859 A1 | 7/1999 |
| WO | 9938553 A1 | 8/1999 |
| WO | 9942166 A1 | 8/1999 |
| WO | 0012171 A1 | 3/2000 |
| WO | 0016844 A1 | 3/2000 |
| WO | 00/20050 A1 | 4/2000 |
| WO | 0033901 A1 | 6/2000 |
| WO | 2000033901 A1 | 6/2000 |
| WO | 0123023 A1 | 4/2001 |
| WO | 2001023023 A1 | 4/2001 |
| WO | 0160444 A1 | 8/2001 |
| WO | 01/70304 A1 | 9/2001 |
| WO | 2001095813 | 12/2001 |
| WO | 0247549 A1 | 6/2002 |
| WO | 2002047549 A1 | 6/2002 |
| WO | 03/030962 A2 | 4/2003 |
| WO | 03084832 A1 | 10/2003 |
| WO | 03090509 A2 | 11/2003 |
| WO | 2004004800 A2 | 1/2004 |
| WO | 2004/012787 A2 | 2/2004 |
| WO | 2004028611 A1 | 4/2004 |
| WO | 2004071555 A2 | 8/2004 |
| WO | 2004091434 A2 | 10/2004 |
| WO | 2005037055 A2 | 4/2005 |
| WO | 2005068009 A1 | 7/2005 |
| WO | 2005072627 A1 | 8/2005 |
| WO | 2005/089833 A1 | 9/2005 |
| WO | 2006078915 A2 | 7/2006 |
| WO | 2006096686 A1 | 9/2006 |
| WO | 2006116438 A2 | 11/2006 |
| WO | 2006116613 A1 | 11/2006 |
| WO | 2006130133 A1 | 12/2006 |
| WO | 2006134100 A1 | 12/2006 |
| WO | 2007041471 A2 | 4/2007 |
| WO | 2007079024 A2 | 7/2007 |
| WO | 2007092210 A1 | 8/2007 |
| WO | 2007094898 A2 | 8/2007 |
| WO | 2007098771 A2 | 9/2007 |
| WO | 2007109164 A2 | 9/2007 |
| WO | 2007126645 A2 | 11/2007 |
| WO | 2007136538 A2 | 11/2007 |
| WO | 2008008126 A2 | 1/2008 |
| WO | 2008/024440 A1 | 2/2008 |
| WO | 2008019236 A1 | 2/2008 |
| WO | 2008048361 A1 | 4/2008 |
| WO | 2008062173 A1 | 5/2008 |
| WO | 2008063226 A2 | 5/2008 |
| WO | 2008147760 A1 | 12/2008 |
| WO | 2008157763 A1 | 12/2008 |
| WO | 2009002839 A1 | 12/2008 |
| WO | 2009012385 A1 | 1/2009 |
| WO | 2009012395 A1 | 1/2009 |
| WO | 2009035582 A1 | 3/2009 |
| WO | 2009046439 A2 | 4/2009 |
| WO | 2009046725 A1 | 4/2009 |
| WO | 2009108669 A1 | 9/2009 |
| WO | 2010030351 A1 | 3/2010 |
| WO | 2010062633 A1 | 6/2010 |
| WO | 2010118144 A1 | 10/2010 |
| WO | 2011046604 A2 | 4/2011 |
| WO | 2011053499 A1 | 5/2011 |
| WO | 2011056619 A1 | 5/2011 |
| WO | 2011062750 A1 | 5/2011 |
| WO | 2011133950 A1 | 10/2011 |
| WO | 2011146649 A1 | 11/2011 |
| WO | 2013/165935 A1 | 11/2013 |
| WO | 2014031763 A2 | 2/2014 |

OTHER PUBLICATIONS

U.S. Appl. No. 12/796,133, filed Jun. 8, 2010 Notice of Allowance dated Jun. 9, 2011.
U.S. Appl. No. 12/917,323, filed Nov. 1, 2010 Advisory Action dated Apr. 10, 2013.
U.S. Appl. No. 12/917,323, filed Nov. 1, 2010 Final Office Action dated Jan. 29, 2013.
U.S. Appl. No. 12/917,323, filed Nov. 1, 2010 Non-Final Office Action dated Aug. 15, 2012.
U.S. Appl. No. 12/917,323, filed Nov. 1, 2010 Non-Final Office Action dated Aug. 26, 2014.
U.S. Appl. No. 12/917,323, filed Nov. 1, 2010 Notice of Allowance dated Jan. 21, 2015.
U.S. Appl. No. 12/419,854, filed Apr. 7, 2009 Non-Final Office Action dated Aug. 5, 2011.
U.S. Appl. No. 13/110,734, filed May 18, 2011 Non-Final Office Action dated Jul. 7, 2014.
U.S. Appl. No. 13/113,834, filed May 23, 2011 Final Office Action dated Nov. 23, 2012.
U.S. Appl. No. 13/113,834, filed May 23, 2011 Non-Final Office Action dated Jul. 17, 2012.
U.S. Appl. No. 13/159,230, filed Jun. 13, 2011 Notice of Allowance dated Aug. 1, 2012.
U.S. Appl. No. 13/250,909, filed Sep. 30, 2011 Notice of Allowance dated Aug. 6, 2012.
U.S. Appl. No. 13/438,586, filed Apr. 3, 2012 Advisory Action dated May 29, 2013.
U.S. Appl. No. 13/438,586, filed Apr. 3, 2012 Final Office Action dated Mar. 7, 2013.
U.S. Appl. No. 13/438,586, filed Apr. 3, 2012 Non-Final Office Action dated Sep. 19, 2012.
U.S. Appl. No. 13/438,586, filed Apr. 3, 2012 Notice of Allowance dated Sep. 16, 2013.
U.S. Appl. No. 13/471,219, filed May 14, 2012 Non-Final Office Action dated Jul. 10, 2013.
U.S. Appl. No. 13/524,712, filed Jun. 15, 2012 Advisory Action dated May 7, 2014.
U.S. Appl. No. 13/524,712, filed Jun. 15, 2012 Final Office Action dated Mar. 3, 2014.
U.S. Appl. No. 13/524,712, filed Jun. 15, 2012 Non-Final Office Action dated Aug. 21, 2014.
U.S. Appl. No. 13/524,712, filed Jun. 15, 2012 Non-Final Office Action dated Oct. 22, 2013.
U.S. Appl. No. 13/524,712, filed Jun. 15, 2012 Notice of Allowance dated Dec. 12, 2014.
U.S. Appl. No. 13/571,088, filed Aug. 9, 2012 Final Office Action dated Jul. 16, 2013.
U.S. Appl. No. 13/571,088, filed Aug. 9, 2012 Final Office Action dated Jul. 6, 2015.
U.S. Appl. No. 13/571,088, filed Aug. 9, 2012 Non-Final Office Action dated Feb. 27, 2013.
U.S. Appl. No. 13/571,088, filed Aug. 9, 2012 Non-Final Office Action dated Jan. 7, 2015.
U.S. Appl. No. 13/571,088, filed Aug. 9, 2012 Notice of Allowance dated Sep. 16, 2015.
U.S. Appl. No. 13/776,451, filed Feb. 25, 2013 Non-Final Office Action dated Jul. 24, 2013.
U.S. Appl. No. 13/776,517, filed Feb. 25, 2013 Final Office Action dated Jun. 30, 2014.
U.S. Appl. No. 13/776,517, filed Feb. 25, 2013 Non-Final Office Action dated Feb. 27, 2014.
U.S. Appl. No. 13/776,517, filed Feb. 25, 2013 Non-Final Office Action dated Nov. 15, 2013.
U.S. Appl. No. 13/776,517, filed Feb. 25, 2013 Notice of Allowance dated Sep. 23, 2014.

(56) References Cited

OTHER PUBLICATIONS

U.S. Appl. No. 13/801,893, filed Mar. 13, 2013 Notice of Allowance dated Sep. 24, 2015.
U.S. Appl. No. 13/853,942, filed Mar. 29, 2013 Non-Final Office Action dated Jul. 26, 2013.
U.S. Appl. No. 13/853,956, filed Mar. 29, 2013 Final Office Action dated Feb. 20, 2015.
U.S. Appl. No. 13/853,956, filed Mar. 29, 2013 Final Office Action dated Jan. 10, 2017.
U.S. Appl. No. 13/853,956, filed Mar. 29, 2013 Final Office Action dated Oct. 18, 2016.
U.S. Appl. No. 13/853,956, filed Mar. 29, 2013 Non-Final Office Action dated Dec. 3, 2013.
U.S. Appl. No. 13/853,956, filed Mar. 29, 2013 Non-Final Office Action dated Jun. 16, 2016.
U.S. Appl. No. 13/853,956, filed Mar. 29, 2013 Non-Final Office Action dated Sep. 15, 2014.
U.S. Appl. No. 13/853,961, filed Mar. 29, 2013 Final Office Action dated Feb. 20, 2015.
U.S. Appl. No. 13/853,961, filed Mar. 29, 2013 Final Office Action dated Jan. 9, 2017.
U.S. Appl. No. 13/853,961, filed Mar. 29, 2013 Non-Final Office Action dated Dec. 3, 2013.
U.S. Appl. No. 13/853,961, filed Mar. 29, 2013 Non-Final Office Action dated Jun. 15, 2016.
U.S. Appl. No. 13/853,961, filed Mar. 29, 2013 Non-Final Office Action dated Oct. 18, 2016.
U.S. Appl. No. 13/853,961, filed Mar. 29, 2013 Non-Final Office Action dated Sep. 12, 2014.
U.S. Appl. No. 13/972,538, filed Aug. 21, 2013 Non-Final Office Action dated Feb. 3, 2016.
U.S. Appl. No. 14/083,250, filed Nov. 18, 2013 Non-Final Office Action dated Dec. 12, 2016.
U.S. Appl. No. 14/083,250, filed Nov. 18, 2013 Non-Final Office Action dated Apr. 1, 2016.
U.S. Appl. No. 11/380,124, filed Apr. 25, 2006 Notice of Allowance dated Apr. 29, 2013.
U.S. Appl. No. 11/380,621, filed Apr. 27, 2006 Final Office Action dated Jan. 14, 2010.
U.S. Appl. No. 11/380,621, filed Apr. 27, 2006 Final Office Action dated Jan. 23, 2009.
U.S. Appl. No. 11/380,621, filed Apr. 27, 2006 Final Office Action dated Mar. 8, 2011.
U.S. Appl. No. 11/380,621, filed Apr. 27, 2006 Non-Final Office Action dated Jul. 1, 2009.
U.S. Appl. No. 11/380,621, filed Apr. 27, 2006 Non-Final Office Action dated Jun. 6, 2008.
U.S. Appl. No. 11/725,287, filed Mar. 19, 2007 Non-final Office Action dated Dec. 3, 2008.
U.S. Appl. No. 11/725,287, filed Mar. 19, 2007 Non-final Office Action dated Jun. 12, 2009.
U.S. Appl. No. 11/725,287, filed Mar. 19, 2007 Non-final Office Action dated Mar. 29, 2010.
U.S. Appl. No. 11/937,302, filed Nov. 8, 2007 Final Office Action dated Nov. 8, 2012.
U.S. Appl. No. 11/937,302, filed Nov. 8, 2007 Final Office Action dated Oct. 13, 2011.
U.S. Appl. No. 11/937,302, filed Nov. 8, 2007 Non-Final Office Action dated Jun. 18, 2012.
U.S. Appl. No. 11/937,302, filed Nov. 8, 2007 Final Office Action dated Feb. 11, 2011.
U.S. Appl. No. 11/937,302, filed Nov. 8, 2007 Non-Final Office Action dated Apr. 15, 2011.
U.S. Appl. No. 11/937,302, filed Nov. 8, 2007 Non-Final Office Action dated Sep. 13, 2010.
U.S. Appl. No. 12/023,280, filed Jan. 31, 2008 Final Office Action dated Mar. 9, 2010.
U.S. Appl. No. 12/023,280, filed Jan. 31, 2008 Non-Final Office Action dated Dec. 13, 2010.
U.S. Appl. No. 12/023,280, filed Jan. 31, 2008 Non-Final Office Action dated Jul. 23, 2009.
U.S. Appl. No. 12/023,280, filed Jan. 31, 2008 Non-Final Office Action dated Oct. 5, 2009.
U.S. Appl. No. 12/023,280, filed Jan. 31, 2008 Notice of Allowance dated Mar. 28, 2011.
U.S. Appl. No. 12/143,377, filed Jun. 20, 2008 Final Office Action dated Oct. 19, 2009.
U.S. Appl. No. 12/143,377, filed Jun. 20, 2008 Non-final Office Action dated Apr. 27, 2009.
U.S. Appl. No. 12/175,182, filed Jul. 17, 2008 Non-final Office Action dated Sep. 3, 2009.
U.S. Appl. No. 12/267,160, filed Nov. 7, 2008 Examiner's Answer dated Dec. 5, 2012.
U.S. Appl. No. 12/267,160, filed Nov. 7, 2008 Final Office Action dated Jun. 1, 2012.
U.S. Appl. No. 12/267,160, filed Nov. 7, 2008 Non-Final Office Action dated Nov. 1, 2011.
U.S. Appl. No. 12/419,854, filed Apr. 7, 2009 Advisory Action dated May 17, 2013.
U.S. Appl. No. 12/419,854, filed Apr. 7, 2009 Final Office Action dated Feb. 14, 2013.
U.S. Appl. No. 12/419,854, filed Apr. 7, 2009 Final Office Action dated Nov. 29, 2011.
U.S. Appl. No. 12/419,854, filed Apr. 7, 2009 Non-Final Office Action dated Jun. 26, 2012.
U.S. Appl. No. 12/419,854, filed Apr. 7, 2009 Notice of Allowance dated Apr. 7, 2014.
U.S. Appl. No. 12/419,957, filed Apr. 7, 2009 Advisory Action dated Feb. 18, 2011.
U.S. Appl. No. 12/419,957, filed Apr. 7, 2009 Final Office Action dated Dec. 7, 2010.
U.S. Appl. No. 12/419,957, filed Apr. 7, 2009 Non-Final Office Action dated Feb. 18, 2010.
U.S. Appl. No. 12/419,957, filed Apr. 7, 2009 Non-Final Office Action dated Jul. 29, 2010.
U.S. Appl. No. 12/419,957, filed Apr. 7, 2009 Non-Final Office Action dated Jun. 30, 2009.
U.S. Appl. No. 12/419,957, filed Apr. 7, 2009 Notice of Allowance dated Mar. 7, 2011.
U.S. Appl. No. 12/420,007, filed Apr. 7, 2009 Final Office Action dated Mar. 22, 2013.
U.S. Appl. No. 12/420,007, filed Apr. 7, 2009 Non-Final Office Action dated Oct. 16, 2012.
U.S. Appl. No. 12/420,007, filed Apr. 7, 2009 Final Office Action dated Feb. 18, 2010.
U.S. Appl. No. 12/420,007, filed Apr. 7, 2009 Non-Final Office Action dated Jul. 14, 2009.
U.S. Appl. No. 12/420,028, filed Apr. 7, 2009 Non-Final Office Action dated Jan. 5, 2011.
U.S. Appl. No. 12/420,028, filed Apr. 7, 2009 Notice of Allowance dated Apr. 1, 2011.
U.S. Appl. No. 12/617,981, filed Nov. 13, 2009 Final Office Action dated Aug. 2, 2012.
U.S. Appl. No. 12/617,981, filed Nov. 13, 2009 Advisory Action dated Sep. 15, 2011.
U.S. Appl. No. 12/617,981, filed Nov. 13, 2009 Final Office Action dated Jun. 21, 2011.
U.S. Appl. No. 12/617,981, filed Nov. 13, 2009 Non-Final Office Action dated Dec. 21, 2011.
U.S. Appl. No. 12/617,981, filed Nov. 13, 2009 Non-Final Office Action dated Jan. 5, 2011.
Smiths Medical, "Smiths Medical Launches Implantable Ports for Easy Viewing Under CT Scans" Press Release, Jan. 5, 2011.
Soloman, et al., "CIN Strategies: Anticipate, Manage, Prevent." Supplement to Imaging Economics, May 2007.
Statement of Prof. Dr. med. Karl R. Aigner, Oct. 11, 2011.
Steinbach, Barbara G. , Hardt, N. Sisson, Abbitt, Patricia L., Lanier, Linda, Caffee, H. Hollis, "Breast Implants, Common Complications, and Concurrent Breast Disease." RadioGraphics, vol. 13, No. 1, pp. 95-118, 1993.
Sullivan et al. "Radiopaque Markers on Mammary Implants." American Journal of Roentgenology 153(2):428, Aug. 1989.

(56) References Cited

OTHER PUBLICATIONS

Summers, "A New and Growing family of artificial implanted fluid-control devices" vol. XVI Trans. Amer. Soc. Artif. Int. Organs, 1970.
Takeuchi, Syuhei et al., "Safety Considerations in the Power Injection of Contrast Medium via a Totally Implantable Central Venous Access System," Japan Journal of Interventional Radiology vol. 20, No. 1, pp. 27-30, Jan. 2005.
Tilford, C. R., "Pressure and Vacuum Measurements"—Ch 2 of Physical Methods of Chemistry pp. 101-173, 1992.
foray "P-U Celsite Port" brochure—Sep. 1999.
U.S. Department of Health and Human Services, FDA, "Labeling: Regulatory Requirements for Medical Devices" Aug. 1989.
U.S. Food and Drug Administration, "Guidance for Institutional Review Boards and Clinical Investigators 1998 Update: Medical Devices." Version Sep. 10, 2008.
U.S. Appl. No. 60/658,518, filed Mar. 4, 2005, publicly accessible Oct. 5, 2006.
Urquiola, Javier, et al., "Using Lead Foil as a Radiopaque Marker for Computerized Tomography Imaging When Implant Treatment Planning." The Journal of Prosthetic Dentistry, 1997.
U.S. Appl. No. 10/374,000, filed Feb. 25, 2003 Office Action dated Aug. 28, 2007.
U.S. Appl. No. 10/374,000, filed Feb. 25, 2003 Advisory Action dated Jan. 23, 2007.
U.S. Appl. No. 10/374,000, filed Feb. 25, 2003 Non-Final Office Action dated Feb. 13, 2006.
U.S. Appl. No. 10/374,000, filed Feb. 25, 2003 Non-Final Office Action dated May 20, 2009.
U.S. Appl. No. 10/374,000, filed Feb. 25, 2003 Non-final Office Action dated Mar. 20, 2008.
U.S. Appl. No. 10/374,000, filed Feb. 25, 2003 Office Action dated Feb. 28, 2007.
U.S. Appl. No. 10/374,000, filed Feb. 25, 2003 Office Action dated Jul. 28, 2006.
U.S. Appl. No. 10/374,000, filed Feb. 25, 2003 Office Action dated Sep. 30, 2008.
U.S. Appl. No. 10/374,000, filed Feb. 25, 2003 Response to Non-Final Office Action dated May 12, 2006.
U.S. Appl. No. 10/374,000, filed Feb. 25, 2003 Response to Office Action dated Dec. 28, 2006.
U.S. Appl. No. 10/374,000, filed Feb. 25, 2003 Response to Office Action dated Jun. 20, 2008.
U.S. Appl. No. 10/374,000, filed Feb. 25, 2003 Response to Office Action dated Mar. 30, 2009.
U.S. Appl. No. 10/374,000, filed Feb. 25, 2003 Response to Office Action dated May 28, 2007.
U.S. Appl. No. 10/374,000, filed Feb. 25, 2003 Response to Office Action dated Nov. 28, 2006.
U.S. Appl. No. 10/374,000, filed Feb. 25, 2003 Response to Office Action dated Oct. 31, 2007.
U.S. Appl. No. 10/374,000, filed Feb. 25, 2003 Response to Office Action dated Sep. 21, 2009.
U.S. Appl. No. 11/320,223, filed Dec. 28, 2005 Advisory Action dated Dec. 1, 2011.
U.S. Appl. No. 11/320,223, filed Dec. 28, 2005 Notice of Allowance dated Jan. 6, 2012.
U.S. Appl. No. 11/320,223, filed Dec. 28, 2005 Final Office Action dated Aug. 3, 2011.
U.S. Appl. No. 11/320,223, filed Dec. 28, 2005 Final Office Action dated Jun. 19, 2009.
U.S. Appl. No. 11/320,223, filed Dec. 28, 2005 Final Office Action dated Jun. 22, 2010.
U.S. Appl. No. 11/320,223, filed Dec. 28, 2005 Non-Final Office Action dated Feb. 13, 2008.
U.S. Appl. No. 11/320,223, filed Dec. 28, 2005 Non-Final Office Action dated Jan. 21, 2010.
U.S. Appl. No. 11/320,223, filed Dec. 28, 2005 Non-Final Office Action dated Mar. 16, 2011.
U.S. Appl. No. 11/320,223, filed Dec. 28, 2005 Non-Final Office Action dated Sep. 18, 2008.
U.S. Appl. No. 11/368,954, filed Mar. 6, 2006 Non-Final Office Action dated Jul. 21, 2009.
U.S. Appl. No. 11/368,954, filed Mar. 6, 2006 Notice of Allowance dated Jun. 24, 2010.
U.S. Appl. No. 11/368,954, filed Mar. 6, 2006 Final Office Action dated Jan. 27, 2010.
U.S. Appl. No. 11/368,954, filed Mar. 6, 2006 Supplemental Non-final Office Action dated Oct. 2, 2009.
U.S. Appl. No. 11/380,124, filed Apr. 25, 2006 Final Office Action dated Aug. 13, 2010.
U.S. Appl. No. 11/380,124, filed Apr. 25, 2006 Final Office Action dated Oct. 20, 2011.
U.S. Appl. No. 11/380,124, filed Apr. 25, 2006 Final Office Action dated Sep. 21, 2009.
U.S. Appl. No. 11/380,124, filed Apr. 25, 2006 Non-Final Office Action dated Apr. 26, 2010.
U.S. Appl. No. 11/380,124, filed Apr. 25, 2006 Non-Final Office Action dated Apr. 7, 2011.
U.S. Appl. No. 11/380,124, filed Apr. 25, 2006 Non-Final Office Action dated Jan. 16, 2009.
U.S. Appl. No. 11/380,124, filed Apr. 25, 2006 Non-Final Office Action dated Oct. 28, 2010.
CN 200980153471.3 filed Jun. 30, 2011 Third Office Action dated May 28, 2014.
CN 201080020088.3 filed Nov. 7, 2011 First Office Action dated Mar. 4, 2013.
CN 201080020088.3 filed Nov. 7, 2011 Second Office Action dated Nov. 21, 2013.
CN 201080051911.7 filed May 16, 2012 First Office Action dated Dec. 27, 2013.
CN 201080051911.7 filed May 16, 2012 Second Office Action dated Jul. 16, 2014.
CN 201080051911.7 filed May 16, 2012 Third Office Action dated Jan. 30, 2015.
CN 201380016157.7 filed Sep. 23, 2014 First office action dated May 16, 2016.
CN 201380016157.7 filed Sep. 23, 2014 Office Action dated Feb. 4, 2017.
CN 201410216386.X filed May 21, 2014 First Office Action dated Nov. 2, 2015.
CN 201410216386.X filed May 21, 2014 Office Action dated Jun. 24, 2016.
CN 201410216386.X filed May 21, 2014 Office Action dated Nov. 29, 2016.
CN 201410216386.X filed May 21, 2014 Search Report dated Nov. 2, 2015.
CO 14.235.202 filed Oct. 23, 2014 Office Action dated Apr. 25, 2017.
CO 14.235.202 filed Oct. 23, 2014 Office Action dated Nov. 3, 2016.
Cook Vital-Port® Product Catalog (2000).
Costa, Nancy, "More Than Skin Deep: An Overview of Iodinated Contrast Media . . . " Journal for the Association for Vascular Access, vol. 8, No. 4, 2003.
Costa, Nancy, "Understanding Contrast Media." Journal of Infusion Nursing, vol. 27, No. 5, Sep./Oct. 2004.
Council Directive 93/42/EEC of Jun. 14, 1993 concerning medical devices (Jun. 14, 1993).
Coyle, Douglas et al, Power Injection of Contrast Media via Peripherally Inserted Central Catheters for CT, J Vasc Interv Radiol, pp. 809-814, vol. 15, 2004.
Deltec Port Systems (Feb. and Apr. 1996).
Department of Health and Human Services, C-Port 510(k) FDA Clearance, Jun. 5, 2003.
Department of Health and Human Services, PowerPort 510(k) FDA Clearance, Jan. 25, 2007.
Desmeules et al. "Venous Access for Chronic Hemodialysis: 'Undesirable Yet Unavoidable'", Artificial Organs 28(7):611-616 (2004).
ECRI Institute, Healthcare Product Comparison System, Dec. 2007.
EP 06 751 411.7 filed Apr. 25, 2006 Office Action dated Sep. 2, 2008.

(56) References Cited

OTHER PUBLICATIONS

EP 06737222.7 filed Aug. 17, 2007 Office Action dated Jul. 27, 2016.
EP 06737222.7 filed Aug. 17, 2007 Office Action dated Mar. 9, 2017.
EP 06751411 filed Apr. 25, 2006 Decision of the Technical Board of Appeal dated Jul. 24, 2013.
EP 06751411 filed Apr. 25, 2006 Decision Revoking the European Patent dated Aug. 1, 2012.
EP 06751411 filed Apr. 25, 2006 Office Action dated Aug. 10, 2009.
EP 06751411 filed Apr. 25, 2006 Opposition by Aesculap AG dated Oct. 6, 2011.
EP 06751411 filed Apr. 25, 2006 Opposition by Fresenius Kabi Deutschland GmbH dated Oct. 11, 2011.
EP 06751411 filed Apr. 25, 2006 Opposition by pfm medical ag dated Oct. 18, 2011.
EP 06751664.1 filed Apr. 27, 2006 First Examination Report dated Jul. 11, 2013.
EP 06751664.1 filed Apr. 27, 2006 Second Examination Report dated Dec. 17, 2014.
EP 06845998 filed Dec. 21, 2006 Office Action dated Mar. 10, 2011.
EP 06845998 filed Dec. 21, 2006 Supplementary Search Report dated Jul. 22, 2010.
EP 06845998.1 filed Dec. 21, 2006 Examination Report dated Feb. 6, 2014.
EP 06845998.1 filed Dec. 21, 2006 Examination Report dated May 13, 2013.
EP 06845998.1 filed Dec. 21, 2006 Examination Report dated Nov. 7, 2012.
EP 06845998.1 filed Dec. 21, 2006 Summons for Oral Proceedings dated Sep. 30, 2014.
EP 10 831 973.2 filed May 30, 2012 Extended European Search Report dated Jul. 4, 2014.
EP 10183380.4 filed Apr. 25, 2006 European Search Report dated May 22, 2013.
EP 10183382.0 filed Apr. 25, 2006 European Search Report dated May 22, 2013.
EP 10183382.0 filed Apr. 25, 2006 Intent to Grant dated Mar. 7, 2014.
EP 10183394.5 filed Apr. 25, 2006 European Search Report dated May 22, 2013.
EP 10183394.5 filed Apr. 25, 2006 interlocutory decision dated Feb. 14, 2017.
EP 10183394.5 filed Apr. 25, 2006 Opposition by Smiths Medical ASD, Inc. dated Apr. 25, 2014.
EP 10183398.6 filed Apr. 25, 2006 European Search Report dated May 22, 2013.
EP 10762377.9 filed Oct. 5, 2011 European Search Report dated Aug. 3, 2012.
EP 10762377.9 filed Oct. 5, 2011 Office Action dated Jul. 17, 2013.
EP 11784194.0 filed Nov. 29, 2012 Examination report dated Jul. 5, 2016.
EP 11784194.0 filed Nov. 29, 2012 extended European search report dated Feb. 21, 2014.
EP 13158343.7 filed Mar. 8, 2013 Examination Report dated Feb. 4, 2014.
EP 13158343.7 filed Mar. 8, 2013 Extended European Search Report dated May 14, 2013.
EP 13158343.7 filed Mar. 8, 2013 Summons to Attend Oral Proceedings dated Oct. 20, 2014.
EP 13764254.2 filed Sep. 10, 2014 Extended European Search Report dated Feb. 19, 2016.
EP 13764254.2 filed Sep. 10, 2014 Partial European Search Report dated Oct. 14, 2015.
EP 13830592.5 filed Feb. 24, 2015 Extended European Search Report dated Mar. 21, 2016.
EP 14198524.2 filed Dec. 17, 2014 Extended European Search Report dated Sep. 14, 2015.
EP 15180174 filed Aug. 7, 2015 European Search Report dated Jan. 4, 2016.
EP 15180174 filed Aug. 7, 2015 Office Action dated Jan. 13, 2017.
EP 2 324 879 filed Apr. 25, 2006 Opposition by Smiths Medical ASD, Inc. dated Dec. 2, 2015.
EP 99 964 086.5 filed Dec. 3, 1999 Office Action dated Dec. 15, 2005.
EP 99 964 086.5 filed Dec. 3, 1999 Office Action dated Mar. 1, 2005.
EP 99 964 086.5 filed Dec. 3, 1999 Office Action dated Mar. 30, 2005.
Ethanol Lock Technique for Prevention and Treatment of Central line-Associated Bloodstream Infections (Nebraska) Aug. 13, 2011, Accessed: Jun. 29, 2013 http://www.nebraskamed.com/app_files/pdf/careers/education-programs/asp/tnmc_etohlock_final.pdf.
Extravasation of Radiologic Contrast, PA-PSRS Patient Safety Advisory, vol. 1 No. 3, Sep. 2004.
Extreme Access™ Bard Access Systems, Inc. Product Brochure, 2003.
Fallscheer, et al., "Injury to the Upper Extremity Cuased by Extravasation of Contrast Medium: A True Emergency." Scandinavian Journal of Plastic and Reconstructive Surgery and Hand Surgery, vol. 41, pp. 26-32, 2007.
Fresenius Brochure on Intraport 1, Intraport II, and Bioport (Nov. 1998).
Gebauer, B. et al., "Contrast Media Power Injection Using Central Venous Port Catheters—Results of an In-Vitro Study," Experimental Radiology 2005: 177: 1417-1423.
Gebauer, B. et al., "Contrast Media Power Injection Using Central Venous Port Catheters—Results of an In-Vitro Study," Experimental Radiology 2005: 177: 1417-1423.—Translation.
HMO 2002 Product Catalog, 2002.
Hou, Shaw-Min et al. "Comparisons of Outcomes and Survivals for Two Central Venous Access Port Systems." Journal of Surgical Oncology, 91:61-66, 2005.
Inamed Health, BioEnterics® LAP-BAND® "Adjustable Gastric Banding System" Product Brochure, Dec. 2003.
Johnson, Kathleen A., "Power Injectable Portal Systems." Journal of Radiology Nursing, vol. 28, Issue 1, Mar. 2009.
JP 2007-558331 filed Mar. 6, 2006 Office Action dated Aug. 20, 2013.
JP 2007-558331 filed Mar. 6, 2006 Office Action dated Jan. 22, 2013.
JP 2007-558331 filed Mar. 6, 2006 Office Action dated May 17, 2011.
JP 2008-509056 filed Apr. 25, 2006 Office Action dated Apr. 4, 2012.
JP 2008-509056 filed Apr. 25, 2006 Office Action dated Jun. 7, 2011.
JP 2012-156976 filed Jul. 12, 2012 Notice of Reasons for Refusal dated Apr. 8, 2014.
JP 2012-156976 filed Jul. 12, 2012 Notice of Reasons for Refusal dated Aug. 27, 2013.
JP 2012-156976 filed Jul. 12, 2012 Office Action dated Jun. 28, 2016.
JP 2012-156976 filed Jul. 12, 2012 Submission of Documents by Third Party dated May 14, 2013.
JP 2012-156976 filed Mar. 6, 2006, Office Action dated Mar. 29, 2016.
JP 2012-156976 filed Mar. 6, 2006, Third Party Submission dated Jul. 29, 2015.
JP 2012-504826 filed Oct. 6, 2011 First Office Action dated Mar. 4, 2014.
JP 2012-504826 filed Oct. 6, 2011 Second Office Action dated Nov. 17, 2014.
JP 2013-209156 filed Oct. 4, 2013 Non-Final Office Action dated Oct. 7, 2014.
JP 2013-511339 filed Nov. 16, 2012 First Office Action dated Feb. 19, 2015.
JP 2013-511339 filed Nov. 16, 2012 Office Action and Pre-Appeal Report dated Apr. 12, 2016.
JP 2013-511339 filed Nov. 16, 2012 Office Action dated Dec. 16, 2016.
JP 2013-511339 filed Nov. 16, 2012 Second Office Action dated Oct. 16, 2015.

(56) References Cited

OTHER PUBLICATIONS

JP 2015-501762 filed Sep. 16, 2014 First Office Action dated Oct. 5, 2016.
JP 2015-501762 filed Sep. 16, 2014 Office Action dated Feb. 1, 2017.
JP 2016-026954 filed Feb. 16, 2016 Office Action dated Dec. 15, 2016.
Kaste et al., "Safe use of power injectors with central and peripheral venous access devices for pediatric CT," Pediatr Radiol (1996) 26: 499-501.
Allergan, Inc. LAP-BAND® System Fact Sheet. © 2007.
AngioDynamics, Smart Port Guidelines for Health Care Providers, 2010.
B. Braun, Access Port Systems, Celsite® Product Information, 19 pages, Nov. 2005.
B. Braun, Easypump Product Page, accessed May 11, 2011.
B. Braun, Port Catheter Systems Product Page, accessed May 11, 2011.
BARD Access Systems Mar. 21, 1995 Product Release to Market form for "M.R.I. Port with 8 Fr. ChronoFlexÒ Catheter", "M.R.I. Port with 8Fr. ChronoFlex Catheter with Intro-Eze™", "M.R.I. Port with 8. Fr ChronoFlex Catheter and Peel Apart", "M.R.I. Port with 8Fr. ChronoFlex Catheter Demo Kit", Drawings included.
Bard Access Systems, BardPort and X-Port Implanted Ports Brochure, © 2007.
Bard Access Systems, BardPort, SlimPort and X-Port Instructions for Use, May 2003.
Bard Access Systems, BardPort, SlimPort, X-Port Instructions for Use, 24 pages, Oct. 2012.
Bard Access Systems, BardPort™ Implanted Ports Patient Information, Feb. 1993.
Bard Access Systems, Devices for Small Patients, 4 pages, Jul. 1992.
Bard Access Systems, Family of PICCs, 1 page, Mar. 10, 2006.
Bard Access Systems, M.R.I. Dual Port with Septum-Finder Ridge IFU, 2 pages, © 1993.
Bard Access Systems, Ports Brochure, © 2003.
Bard Access Systems, PowerPort and PowerLoc CT Guide, 11 pages, Dec. 2009.
Bard Access Systems, PowerPort and PowerLoc Product Brochure, 6 pages, © 2007.
Bard Access Systems, PowerPort CT Guide, 16 pages, Mar. 2007.
Bard Access Systems, PowerPort Guidelines for CT Technologists, 1 page, Feb. 2007.
Bard Access Systems, PowerPort Guidelines for CT Technologists, 1 page, Jul. 2006.
Bard Access Systems, PowerPort Guidelines for Nurses, 1 page, Feb. 2007.
Bard Access Systems, PowerPort Guidelines for Physicians, 1 page, Feb. 2007.
Bard Access Systems, PowerPort Implanted Port with Open-Ended Catheter Instructions for Use, 8 pages, Dec. 2006.
Bard Access Systems, PowerPort Information for the Patient, 5 pages, © 2006.
Bard Access Systems, PowerPort Prescription Pad, 1 page, © 2007.
Bard Access Systems, PowerPort Product Brochure, 8 pages, © 2009.
Bard Access Systems, PowerPort™ Implantable Port Product Information, © 2007.
Bard Access Systems, Titanium Dome Implantable Port, http://www.bardacess.com, last accessed Jan. 10, 2012.
Bard Access Systems, When in Doubt, Scout!, 1 page, © 2007.
Bard Healthcare Leaflet (2001).
BardPort, SlimPort, X-Port Instructions for Use, 2012.
Baxter Guidelines on Port Maintainence (Jun. 2003).
Baxter Healthport® Focus (Oct. 1999).
Baxter Healthport® Venous Systems (Oct. 2002).
Baxter Patient Information, Healthport® System (May 1999).
Baxter Therapy Systems, Baxter Healthport® Jan. 1999.
Beathard et al. "Initial clinical results with the LifeSite Hemodialysis Access System" Kidney International, vol. 58, pp. 2221-2227, (2000).
Biffi, R. et al. "Use of totally implantable central venous access ports for high-dose chemotherapy and peripheral blood stem cell transplantation: results of a monocentre series of 376 patients." Annals of Oncology 15:296-300, 2004.
Biffi, R., et al. "Best Choice of Central Venous Insertion Site for the Prevention of Catheter-Related Complications in Adult Patients Who Need Cancer Therapy: A Randomized Trial." Annals of Oncology, Jan. 29, 2009.
Biffi, Roberto, et al. "A Randomized, Prospective Trial of Central Venous Ports Connected to Standard Open-Ended or Groshong Catheters in Adult Oncology Patients." American Cancer Society, vol. 92, No. 5, pp. 1204-1212, Sep. 1, 2001.
BioEnterics Corporation, LAP-BAND® "Adjustable Gastric Banding System" Product Brochure Rev. G, Nov. 2000.
Biolink: Products—Dialock System (2002).
Biotronik, Stratos Cardiac Resynchronization Therapy Pacemakers Technical Manual, 179 pages, © 2008.
Boston Scientific, Xcela™ Power Injectable PICC Directions for Use, 12 pages, © 2007.
Braun Product Catalog (Aug. 2005).
Buerger et al "Implantation of a new device for haemodialysis" Nephrol. Dial. Transplant 15: 722-724 (2000).
C. R. Bard, Inc. and Bard Peripheral Vascular, Inc., v. Angiodynamics, Inc., C.A. No. 15-218-SLR-SRF, Angiodynamics, Inc.'s Initial Invalidity Contentions dated Jun. 24, 2016.
C.A. No. 15-218-SLR-SRF, Invalidity Contentions Exhibit A1 dated Jun. 24, 2016.
C.A. No. 15-218-SLR-SRF, Invalidity Contentions Exhibit A10 dated Jun. 24, 2016.
C.A. No. 15-218-SLR-SRF, Invalidity Contentions Exhibit A11 dated Jun. 24, 2016.
C.A. No. 15-218-SLR-SRF, Invalidity Contentions Exhibit A12 dated Jun. 24, 2016.
C.A. No. 15-218-SLR-SRF, Invalidity Contentions Exhibit A13 dated Jun. 24, 2016.
C.A. No. 15-218-SLR-SRF, Invalidity Contentions Exhibit A14 dated Jun. 24, 2016.
C.A. No. 15-218-SLR-SRF, Invalidity Contentions Exhibit A15 dated Jun. 24, 2016.
C.A. No. 15-218-SLR-SRF, Invalidity Contentions Exhibit A16 dated Jun. 24, 2016.
C.A. No. 15-218-SLR-SRF, Invalidity Contentions Exhibit A17 dated Jun. 24, 2016.
C.A. No. 15-218-SLR-SRF, Invalidity Contentions Exhibit A18 dated Jun. 24, 2016.
C.A. No. 15-218-SLR-SRF, Invalidity Contentions Exhibit A19 dated Jun. 24, 2016.
C.A. No. 15-218-SLR-SRF, Invalidity Contentions Exhibit A2 dated Jun. 24, 2016.
C.A. No. 15-218-SLR-SRF, Invalidity Contentions Exhibit A20 dated Jun. 24, 2016.
C.A. No. 15-218-SLR-SRF, Invalidity Contentions Exhibit A21 dated Jun. 24, 2016.
C.A. No. 15-218-SLR-SRF, Invalidity Contentions Exhibit A22 dated Jun. 24, 2016.
C.A. No. 15-218-SLR-SRF, Invalidity Contentions Exhibit A23 dated Jun. 24, 2016.
C.A. No. 15-218-SLR-SRF, Invalidity Contentions Exhibit A24 dated Jun. 24, 2016.
C.A. No. 15-218-SLR-SRF, Invalidity Contentions Exhibit A25 dated Jun. 24, 2016.
C.A. No. 15-218-SLR-SRF, Invalidity Contentions Exhibit A26 dated Jun. 24, 2016.
C.A. No. 15-218-SLR-SRF, Invalidity Contentions Exhibit A27 dated Jun. 24, 2016.
C.A. No. 15-218-SLR-SRF, Invalidity Contentions Exhibit A28 dated Jun. 24, 2016.
C.A. No. 15-218-SLR-SRF, Invalidity Contentions Exhibit A29 dated Jun. 24, 2016.

(56) References Cited

OTHER PUBLICATIONS

C.A. No. 15-218-SLR-SRF, Invalidity Contentions Exhibit A3 dated Jun. 24, 2016.
C.A. No. 15-218-SLR-SRF, Invalidity Contentions Exhibit A30 dated Jun. 24, 2016.
C.A. No. 15-218-SLR-SRF, Invalidity Contentions Exhibit A31 dated Jun. 24, 2016.
C.A. No. 15-218-SLR-SRF, Invalidity Contentions Exhibit A32 dated Jun. 24, 2016.
C.A. No. 15-218-SLR-SRF, Invalidity Contentions Exhibit A33 dated Jun. 24, 2016.
C.A. No. 15-218-SLR-SRF, Invalidity Contentions Exhibit A34 dated Jun. 24, 2016.
C.A. No. 15-218-SLR-SRF, Invalidity Contentions Exhibit A35 dated Jun. 24, 2016.
C.A. No. 15-218-SLR-SRF, Invalidity Contentions Exhibit A36 dated Jun. 24, 2016.
C.A. No. 15-218-SLR-SRF, Invalidity Contentions Exhibit A37 dated Jun. 24, 2016.
C.A. No. 15-218-SLR-SRF, Invalidity Contentions Exhibit A38 dated Jun. 24, 2016.
C.A. No. 15-218-SLR-SRF, Invalidity Contentions Exhibit A39 dated Jun. 24, 2016.
C.A. No. 15-218-SLR-SRF, Invalidity Contentions Exhibit A4 dated Jun. 24, 2016.
C.A. No. 15-218-SLR-SRF, Invalidity Contentions Exhibit A40 dated Jun. 24, 2016.
C.A. No. 15-218-SLR-SRF, Invalidity Contentions Exhibit A41 dated Jun. 24, 2016.
C.A. No. 15-218-SLR-SRF, Invalidity Contentions Exhibit A42 dated Jun. 24, 2016.
C.A. No. 15-218-SLR-SRF, Invalidity Contentions Exhibit A43 dated Jun. 24, 2016.
C.A. No. 15-218-SLR-SRF, Invalidity Contentions Exhibit A44 dated Jun. 24, 2016.
C.A. No. 15-218-SLR-SRF, Invalidity Contentions Exhibit A45 dated Jun. 24, 2016.
C.A. No. 15-218-SLR-SRF, Invalidity Contentions Exhibit A46 dated Jun. 24, 2016.
C.A. No. 15-218-SLR-SRF, Invalidity Contentions Exhibit A47 dated Jun. 24, 2016.
C.A. No. 15-218-SLR-SRF, Invalidity Contentions Exhibit A48 dated Jun. 24, 2016.
C.A. No. 15-218-SLR-SRF, Invalidity Contentions Exhibit A49 dated Jun. 24, 2016.
C.A. No. 15-218-SLR-SRF, Invalidity Contentions Exhibit A5 dated Jun. 24, 2016.
C.A. No. 15-218-SLR-SRF, Invalidity Contentions Exhibit A50 dated Jun. 24, 2016.
C.A. No. 15-218-SLR-SRF, Invalidity Contentions Exhibit A51 dated Jun. 24, 2016.
C.A. No. 15-218-SLR-SRF, Invalidity Contentions Exhibit A6 dated Jun. 24, 2016.
C.A. No. 15-218-SLR-SRF, Invalidity Contentions Exhibit A7 dated Jun. 24, 2016.
C.A. No. 15-218-SLR-SRF, Invalidity Contentions Exhibit A8 dated Jun. 24, 2016.
C.A. No. 15-218-SLR-SRF, Invalidity Contentions Exhibit A9 dated Jun. 24, 2016.
C.A. No. 15-218-SLR-SRF, Invalidity Contentions Exhibit B1 dated Jun. 24, 2016.
C.A. No. 15-218-SLR-SRF, Invalidity Contentions Exhibit B10 dated Jun. 24, 2016.
C.A. No. 15-218-SLR-SRF, Invalidity Contentions Exhibit B11 dated Jun. 24, 2016.
KR 10-2011-7026328 filed Nov. 4, 2011 Notice of Last Preliminary Rejection dated Dec. 28, 2016.
KR 10-2011-7026328 filed Nov. 4, 2011 Notice of Preliminary Rejection dated Jun. 20, 2016.
L-CATH® for PORTS, Luther Medical Products, Inc., Tustin, California, 2 pages, 1994.
LaMaitre Vascular "Port Implantations: using the OptiLock Implantable Port," product information, available at http://www.lemaitre.com/specs.pop.asp, last accessed Apr. 2003, 14 pages.
LAP-BAND AP™ "System with Adjustable Gastric Banding system with OMNIFORM™ Design," Product Brochure, Jul. 2007, 16 pages.
LAP-BAND® System Access Port Fill Guide I, "9.75/10.0 cm LAP-BAND System vs. 11 cm LAP-BAND System: For Product Manufactured Prior to Jul. 2001" BioEnterics Corporation. Rev. B. Aug. 15, 2001.
Leslie et al., "A New Simple Power Injector," Am J Roentgenol 128: 381-384, Mar. 1977.
Levin et al. "Initial results of a new access device for hemodialysis" Kidney International, vol. 54, pp. 1739-1745, (1998).
Levin et al. "New Access Device for Hemodialysis", ASAIO Journal (1998).
LifeSite: Instructions for Implantation & Use for the LifeSite Hemodialysis Access System, 2000.
MedComp "PortCT Technology", display at SIR Conference (Mar. 2006), Toronto, Canada.
Medcomp Dialysis and Vascular Access Products (MEDCOMP) Jun. 30, 2009, Accessed Jun. 29, 2013 http://www.medcompnet.com/products/flipbook/pdf/PN2114G_Medcomp_Catalog_pdf.
Medtronic IsoMed Technical Manual, Model 8472, (2008).
Medtronic IsoMed® Constant-Flow Infusion System: Clinical Reference Guide for Hepatic Arterial Infusion Therapy, Revised Sep. 2000.
MX/a/2011/004499 filed Apr. 28, 2011 First Office Action dated Jul. 25, 2013.
MX/a/2011/004499 filed Apr. 28, 2011 Forth Office Action dated Aug. 3, 2015.
Mx/a/2011/004499 filed Apr. 28, 2011 Second Office Action dated May 25, 2014, translation dated Jul. 28, 2014.
MX/a/2011/004499 filed Apr. 28, 2011 Third Office Action dated Jan. 21, 2015.
MX/a/2011/010529 filed Oct. 5, 2011 Office Action dated Jan. 18, 2017.
MX/a/2011/010529 filed Oct. 5, 2011 Office Action dated May 19, 2016.
MX/a/2014/011280 filed Mar. 13, 2013, First Office Action dated May 29, 2015.
MX/a/2014/011280 filed Mar. 13, 2013, Second Office Action dated Oct. 27, 2015.
Navilyst Medical, Implantable Ports with PASV® Valve Technology, Product Overview,<<http://www.navilystmedical.com/Products/index.cfm/9>>last accessed Jun. 4, 2012.
Nebraska Medical Center, Ethanol Lock Technique for Prevention and Treatment of Central Line-Associated Bloodstream Infections, Jul. 2009.
Norfolk Medical Design Dossier/Technical File Vortex, Dec. 1997.
Nucleus Cochlear Implant Systems; User Manual for the ESPrit and ESPrit 22 speech processor and accessories, Issue 3, Apr. 2000.
Nucleus Cochlear Implant Systems; User Manual for the SPrint speech processor and accessories, Issue 4, Apr. 2002.
Oct. 22, 2009 Declaration of Kelly Christian, Director of Product Development at BARD Access Systems, Inc, in support of and depicting a product on the market by Quinton Company approximately ten years prior to Oct. 22, 2009, 1 page.
PCT/US09/62854 filed Oct. 30, 2009 Written Opinion dated Dec. 23, 2009.
PCT/US06/49007 filed Dec. 21, 2006 Search Report and Written Opinion dated Oct. 1, 2007.
PCT/US2006/008022 filed Mar. 6, 2006 International Preliminary Report on Patentability dated Sep. 12, 2007.
PCT/US2006/008022 filed Mar. 6, 2006 Search Report dated Jul. 5, 2006.
PCT/US2006/008022 filed Mar. 6, 2006 Written Opinion dated Apr. 9, 2007.
PCT/US2006/008022 filed Mar. 6, 2006 Written Opinion dated Jul. 5, 2006.

(56) References Cited

OTHER PUBLICATIONS

PCT/US2006/015695 filed Apr. 25, 2006 Partial Search Report dated Sep. 29, 2006.
PCT/US2006/015695 filed Apr. 25, 2006 Search Report dated Jan. 11, 2007.
PCT/US2006/015695 filed Apr. 25, 2006 Written Opinion dated Jan. 11, 2007.
PCT/US2006/016056 filed Apr. 27, 2006 International Preliminary Report on Patentability dated Oct. 30, 2007.
PCT/US2006/016056 filed Apr. 27, 2006 Search Report dated Sep. 20, 2006.
PCT/US2006/016056 filed Apr. 27, 2006 Written Opinion dated Oct. 27, 2007.
PCT/US2006/016056 filed Apr. 27, 2006 Written Opinion dated Sep. 20, 2006.
PCT/US2006/049007 filed Dec. 21, 2006 International Preliminary Report on Patentability dated Jul. 1, 2008.
PCT/US2006/049007 filed Dec. 21, 2006 Written Opinion dated Oct. 1, 2007.
PCT/US2007/006776 filed Mar. 19, 2007 International Preliminary Report on Patentability dated Jan. 2, 2009.
PCT/US2007/006776 filed Mar. 19, 2007 International Search Report dated Dec. 18, 2007.
PCT/US2007/006776 filed Mar. 19, 2007 Written opinion, dated Dec. 18, 2007.
PCT/US2007/011015 dated May 7, 2007 Written Opinion dated Jun. 10, 2008.
PCT/US2007/011015 filed May 7, 2007 International Preliminary Report on Patentability dated Sep. 23, 2008.
C.A. No. 15-218-SLR-SRF, Invalidity Contentions Exhibit B12 dated Jun. 24, 2016.
C.A. No. 15-218-SLR-SRF, Invalidity Contentions Exhibit B13 dated Jun. 24, 2016.
C.A. No. 15-218-SLR-SRF, Invalidity Contentions Exhibit B14 dated Jun. 24, 2016.
C.A. No. 15-218-SLR-SRF, Invalidity Contentions Exhibit B15 dated Jun. 24, 2016.
C.A. No. 15-218-SLR-SRF, Invalidity Contentions Exhibit B16 dated Jun. 24, 2016.
C.A. No. 15-218-SLR-SRF, Invalidity Contentions Exhibit B17 dated Jun. 24, 2016.
C.A. No. 15-218-SLR-SRF, Invalidity Contentions Exhibit B18 dated Jun. 24, 2016.
C.A. No. 15-218-SLR-SRF, Invalidity Contentions Exhibit B19 dated Jun. 24, 2016.
C.A. No. 15-218-SLR-SRF, Invalidity Contentions Exhibit B2 dated Jun. 24, 2016.
C.A. No. 15-218-SLR-SRF, Invalidity Contentions Exhibit B20 dated Jun. 24, 2016.
C.A. No. 15-218-SLR-SRF, Invalidity Contentions Exhibit B21 dated Jun. 24, 2016.
C.A. No. 15-218-SLR-SRF, Invalidity Contentions Exhibit B22 dated Jun. 24, 2016.
C.A. No. 15-218-SLR-SRF, Invalidity Contentions Exhibit B23 dated Jun. 24, 2016.
C.A. No. 15-218-SLR-SRF, Invalidity Contentions Exhibit B24 dated Jun. 24, 2016.
C.A. No. 15-218-SLR-SRF, Invalidity Contentions Exhibit B25 dated Jun. 24, 2016.
C.A. No. 15-218-SLR-SRF, Invalidity Contentions Exhibit B26 dated Jun. 24, 2016.
C.A. No. 15-218-SLR-SRF, Invalidity Contentions Exhibit B27 dated Jun. 24, 2016.
C.A. No. 15-218-SLR-SRF, Invalidity Contentions Exhibit B28 dated Jun. 24, 2016.
C.A. No. 15-218-SLR-SRF, Invalidity Contentions Exhibit B29 dated Jun. 24, 2016.
C.A. No. 15-218-SLR-SRF, Invalidity Contentions Exhibit B3 dated Jun. 24, 2016.
C.A. No. 15-218-SLR-SRF, Invalidity Contentions Exhibit B30 dated Jun. 24, 2016.
C.A. No. 15-218-SLR-SRF, Invalidity Contentions Exhibit B31 dated Jun. 24, 2016.
C.A. No. 15-218-SLR-SRF, Invalidity Contentions Exhibit B32 dated Jun. 24, 2016.
C.A. No. 15-218-SLR-SRF, Invalidity Contentions Exhibit B33 dated Jun. 24, 2016.
C.A. No. 15-218-SLR-SRF, Invalidity Contentions Exhibit B4 dated Jun. 24, 2016.
C.A. No. 15-218-SLR-SRF, Invalidity Contentions Exhibit B5 dated Jun. 24, 2016.
C.A. No. 15-218-SLR-SRF, Invalidity Contentions Exhibit B6 dated Jun. 24, 2016.
C.A. No. 15-218-SLR-SRF, Invalidity Contentions Exhibit B7 dated Jun. 24, 2016.
C.A. No. 15-218-SLR-SRF, Invalidity Contentions Exhibit B8 dated Jun. 24, 2016.
C.A. No. 15-218-SLR-SRF, Invalidity Contentions Exhibit B9 dated Jun. 24, 2016.
C.A. No. 15-218-SLR-SRF, Invalidity Contentions Exhibit C1 dated Jun. 24, 2016.
C.A. No. 15-218-SLR-SRF, Invalidity Contentions Exhibit C2 dated Jun. 24, 2016.
C.A. No. 15-218-SLR-SRF, Invalidity Contentions Exhibit C3 dated Jun. 24, 2016.
C.A. No. 15-218-SLR-SRF, Invalidity Contentions Exhibit C4 dated Jun. 24, 2016.
C.A. No. 15-218-SLR-SRF, Invalidity Contentions Exhibit C5 dated Jun. 24, 2016.
C.A. No. 15-218-SLR-SRF, Invalidity Contentions Exhibit C6 dated Jun. 24, 2016.
CA 2757836 filed Oct. 5, 2011 Examiner's Report dated May 18, 2016.
Canaud et al. "Dialock: a new vascular access device for extracorporeal renal replacement therapy. Preliminary clinical results" Nephrol. Dial. Transplant 14: 692-698 (1999).
Canaud et al. "Dialock: Pilot Trial of a New Vascular Port Access Device for Hemodialysis" Seminars in Dialysis, vol. 12, No. 5, pp. 382-388 (Sep. 1999).
Canaud et al. "Dialock: Results of french multicentar trial" Nephrology, vol. 22, No. 8, pp. 391-397, (2001).
Cardiovascular and Interventional Radiology, Review Article, "Central Venous Access Catheters: Radiological Management of Complications," by U.K. Teichgraber, B. Gebauer, T. Benter, H.J. Wagner, published online Jul. 31, 2003.
Carlson et al., "Safety Considerations in the Power Injection of Contrast Media Via Central Venous Catheters during Computed Tomographic Examinations," Investigative Radiology, (May 1992) 27: 337-340.
Carlson, J. E. et. al., "Safety Considerations in the Power Injection of Contrast Media Via Central Venous Catheters during Computed Tomographic Examinations" Investigative Radiology, vol. 27, p. 337-340, May 1992.
Center for Devices and Radiological Health, Guidance on 510(k) Submissions for Implanted Infusion Ports, Oct. 1990.
Clinical Plastic Products, "Oncology Jet Port Plus Catheter Systems" Instructions for Use, Oct. 12, 2011.
CN 200980153471.3 filed Jun. 30, 2011 Fifth Office Action dated Jun. 2, 2015.
CN 200980153471.3 filed Jun. 30, 2011 First Office Action dated Dec. 25, 2012.
CN 200980153471.3 filed Jun. 30, 2011 Fourth Office Action dated Nov. 15, 2014.
CN 200980153471.3 filed Jun. 30, 2011 Notice of Grant dated Nov. 5, 2015.
CN 200980153471.3 filed Jun. 30, 2011 Second Office Action dated Sep. 18, 2013.
PCT/US2007/011015 filed May 7, 2007 Search Report dated Jun. 10, 2008.
PCT/US2007/011456 filed May 11, 2007 Search Report dated Aug. 28, 2008.

(56) References Cited

OTHER PUBLICATIONS

PCT/US2007/011456 filed May 11, 2007 Written Opinion dated Aug. 28, 2008.
PCT/US2008/010520 dated Sep. 8, 2008 Search Report dated Feb. 24, 2009.
PCT/US2008/010520 filed Sep. 8, 2008 Written Opinion dated Feb. 24, 2009.
PCT/US2008/067679 filed Jun. 20, 2008 Search Report dated Sep. 30, 2008.
PCT/US2008/067679 filed Jun. 20, 2008 Written Opinion dated Sep. 30, 2008.
PCT/US2008/070330 filed Jul. 17, 2008 Search Report dated Dec. 1, 2008.
PCT/US2008/070330 filed Jul. 17, 2008 Written Opinion dated Dec. 1, 2008.
PCT/US2008/070345 filed Jul. 17, 2008 Search Report dated Dec. 1, 2008.
PCT/US2008/070345 filed Jul. 17, 2008 Written Opinion dated Dec. 1, 2008.
PCT/US2008/078976 filed Apr. 2, 2009 Search Report and Written Opinion dated Apr. 3, 2009.
PCT/US2009/035088 filed Feb. 25, 2009 International Search Report dated May 19, 2009.
PCT/US2009/035088 filed Feb. 25, 2009 Written Opinion dated May 19, 2009.
PCT/US2009/062854 filed Oct. 30, 2009 International Preliminary Report on Patentability dated May 5, 2011.
PCT/US2009/062854 filed Oct. 30, 2009 International Search Report dated Dec. 23, 2009.
PCT/US2009/062854 filed Oct. 30, 2009 Search Report dated Dec. 23, 2009.
PCT/US2009/062854 filed Oct. 30, 2009 Written Opinion dated Dec. 23, 2009.
PCT/US2010/030256 filed Apr. 7, 2010 Search Report dated Jun. 4, 2010.
PCT/US2010/030256 filed Apr. 7, 2010 Written Opinion dated Jun. 4, 2010.
PCT/US2010/054994 filed Nov. 1, 2010 Search Report dated Jan. 10, 2011.
PCT/US2010/054994 filed Nov. 1, 2010 Written Opinion dated Jan. 10, 2011.
PCT/US2011/037038 filed May 18, 2011 International Preliminary Report on Patentability dated Nov. 20, 2012.
PCT/US2011/037038 filed May 18, 2011 International Search Report and Written Opinion dated Aug. 30, 2011.
PCT/US2011/037038 filed May 18, 2011 Written Opinion and Search Report dated Aug. 30, 2011.
PCT/US2013/031035 filed Mar. 14, 2013 International Search Report and Written Opinion dated Jun. 3, 2013.
PCT/US2013/056019 filed Aug. 21, 2013 International Search Report and Written Opinion dated Feb. 28, 2014.
PCT/US99/28695 filed Dec. 3, 1999 International Preliminary Examination Report dated Apr. 21, 2001.
PCT/US99/28695 filed Dec. 3, 1999 Search Report dated Apr. 11, 2000.
PFM Medical, Xcela™ Power Injectable Port Directions for Use, 15 pages, © 2008.
Picture of HMP Vortex MP Vascular Access Port from Exhibit A11, Jun. 24, 2016.
Port-A-Cath Implantable Vascular Access Systems, brochure, (1996).
Port-A-Cath® P.A.S. Port® Systems by Deltec, Product Specifications, 1999.
Port-A-Cath® "Implantable Epidural, Aterial and Peritonial Access Systems" Internet Product Listing. <<http://web.archive.org/web/20001119035900/www.deltec.com/cPacspl.htm.>> last accessed Jun. 4, 2012.
Port-A-Cath® "Many Port-A-Cath® System Choices" Product Brochure. © 1996 SIMS Deltec, Inc.
Port-A-Cath® & Port-A-Cath® II Dual-lumen Implantable Venous Access Systems Product Specifications, 2005.
Port-A-Cath® II Implantable Access Systems Information Sheet, Sep. 2006.
Proper Care of the Vortex, Nov. 30, 2000.
Rappolt, Richard T., et al. "Radiopaque Codification and X-ray Identification of Ingested Drugs." Ingestive Radiology, May-Jun. 1966.
Request for Inter partes Reexamination of U.S. Pat. No. 7,785,302, filed Aug. 20, 2012.
Request for Inter partes Reexamination of U.S. Pat. No. 7,947,022, filed Aug. 20, 2012.
Request for Inter partes Reexamination of U.S. Pat. No. 7,959,615, filed Aug. 20, 2012.
Salis et al., "Maximal flow rates possible during power injection through currently available PICCs: An in-vitro study," J Vasc Interv Radiol 2004; 15:275-281.
Sandstede, Joem, "Pediatric CT," available online at www.multislice-ct.com, MultiSLICE-CT.com, version 02, May 2, 2003.
Sanelli, et al., "Safety and Feasibility of Using a Central Venous Catheter for Rapid Contrast Injection Rates." American Journal of Radiology, vol. 183, pp. 1829-1834, Dec. 2004.
Shah, Tilak M., "Radiopaque Polymer Formulations for Medical Devices." Medical Device and Diagnostic Industry, Mar. 2000.
Smith Medical, Port-A-Cath® "Single-lumen Implantable Vascular Access Systems" Product Specifications, 2004.
Smith, Lisa Hartkoph, "Implanted Ports, Computed Tomography, Power Injectors, and Catheter Rupture." Clinical Journal of Oncology Nursing, vol. 12 , No. 5. Oct. 2008.
U.S. Appl. No. 14/104,354, filed Dec. 12, 2013 Final Office Action dated Jun. 21, 2016.
U.S. Appl. No. 14/104,354, filed Dec. 12, 2013 Non-Final Office Action dated Feb. 26, 2016.
U.S. Appl. No. 14/104,354, filed Dec. 12, 2013 Non-Final Office Action dated Nov. 22, 2016.
U.S. Appl. No. 14/141,263, filed Dec. 26, 2013 Notice of Allowance dated Apr. 20, 2016.
U.S. Appl. No. 14/171,364, filed Feb. 3, 2014 Examiner's Answer dated Jul. 29, 2016.
U.S. Appl. No. 14/171,364, filed Feb. 3, 2014 Final Office Action dated Jun. 25, 2015.
U.S. Appl. No. 14/171,364, filed Feb. 3, 2014 Non-Final Office Action dated Feb. 12, 2015.
U.S. Appl. No. 14/455,660, filed Aug. 8, 2014 Final Office Action dated Nov. 27, 2015.
U.S. Appl. No. 14/455,660, filed Aug. 8, 2014 Non-Final Office Action dated Jul. 6, 2015.
U.S. Appl. No. 14/455,660, filed Aug. 8, 2014 Non-Final Office Action dated Mar. 18, 2015.
U.S. Appl. No. 14/455,660, filed Aug. 8, 2014 Non-Final Office Action dated Oct. 14, 2016.
U.S. Appl. No. 14/587,862, filed Dec. 31, 2014 Non-Final Office Action dated Nov. 3, 2016.
U.S. Appl. No. 14/599,376, filed Jan. 16, 2015 Advisory Action dated Aug. 23, 2016.
U.S. Appl. No. 14/599,376, filed Jan. 16, 2015 Final Office Action dated Jun. 8, 2016.
U.S. Appl. No. 14/599,376, filed Jan. 16, 2015 Non-Final Office Action dated Feb. 3, 2016.
U.S. Appl. No. 14/599,376, filed Jan. 16, 2015 Non-Final Office Action dated Nov. 7, 2016.
U.S. Appl. No. 14/750,174, filed Jun. 25, 2015 Non-Final Office Action dated Nov. 1, 2016.
U.S. Appl. No. 14/750,174, filed Jun. 25, 2015 Notice of Allowance dated Mar. 10, 2017.
U.S. Appl. No. 29/239,163, filed Sep. 27, 2005 entitled Injectable Power Port, listing Eddie K. Burnside as inventor.
U.S. Appl. No. 29/247,954, filed Jul. 21, 2006 entitled Injectable Power Port, listing Eddie K. Burnside as inventor.
U.S. Appl. No. 29/247,954, filed Jul. 21, 2006 Non-Final Office Action dated Apr. 6, 2007.
U.S. Appl. No. 29/247,954, filed Jul. 21, 2006 Notice of Allowability dated Jul. 30, 2007.

(56) References Cited

OTHER PUBLICATIONS

U.S. Appl. No. 29/284,454, filed Sep. 7, 2007 titled Implantable Port Device, listing John A. Zawacki and Annmarie Boswell as inventors, in which a Continued Prosecution Application was filed on Jan. 30, 2008.

U.S. Appl. No. 29/284,456, filed Sep. 7, 2007, titled Implantable Port Device, listing John A. Zawacki and Annemarie Boswell as inventors.

U.S. Appl. No. 29/382,235, filed Dec. 30, 2010 Non-Final Office Action dated Oct. 3, 2012.

U.S. Appl. No. 29/382,246, filed Dec. 30, 2010 Notice of Allowance dated Oct. 3, 2012.

U.S. Appl. No. 95/002,089, filed Aug. 20, 2012 Action Closing Prosecution dated Jun. 12, 2013.

U.S. Appl. No. 95/002,089, filed Aug. 20, 2012 Decision on Appeal in U.S. Pat. No. 7,785,302, dated Mar. 11, 2016.

U.S. Appl. No. 95/002,089 filed Aug. 20, 2012 Office Action in and Order Granting/Denying Request for Inter Partes Reexamination dated Nov. 7, 2012.

U.S. Appl. No. 95/002,090, filed Aug. 20, 2012 Action Closing Prosecution dated Jun. 12, 2013.

U.S. Appl. No. 95/002,090, filed Aug. 20, 2012 Decision on Appeal in U.S. Pat. No. 7,947,022, dated Mar. 29, 2016.

U.S. Appl. No. 95/002,090, filed Aug. 20, 2012 Office Action in and Order Granting/Denying Request for Inter Partes Reexamination dated Nov. 7, 2012.

U.S. Appl. No. 95/002,092, filed Aug. 20, 2012 Action Closing Prosecution dated Jun. 12, 2013.

U.S. Appl. No. 95/002,092, filed Aug. 20, 2012 Decision on Appeal in U.S. Pat. No. 7,959,615, dated Mar. 24, 2016.

U.S. Appl. No. 95/002,092, filed Aug. 20, 2012 Office Action in and Order Granting/Denying Request for Inter Partes Reexamination dated Nov. 13, 2012.

Vergara, et al., "Adverse Reactions to Contrast Medica in CT: Effects of Temperature and Ionic Property." Radiology, vol. 199, No. 2, May 1996.

Virot et al. "Long-term use of hemodialysis rooms LifeSite" Nephrologie vol. 24, No. 8, pp. 443-449 (2003).

Vogelzang, Robert L., "Power Injection Through Central Venous Catheters: Physiological and Hemodynamic Considerations." The McGaw Medical Center of Northwestern University, Feinberg School of Medicine. Jun. 23, 2004.

Wells, S. "Venous Access in Oncology and Haematology Patients: Part One." Nursing Standard, vol. 22, No. 52, pp. 39-46, Sep. 3, 2008.

Wikipedia, "Port Catheter", Dec. 15, 2011.

Williamson, et al., "Assessing the Adequacy of Peripherally Inserted Central Catheters for Power Injection of Intravenous Contrast Agents for CT." Journal of Computer Assisted Tomography, vol. 6, No. 6, pp. 932-937, 2001.

U.S. Appl. No. 15/881,616, filed Jan. 26, 2018 Final Office Action dated Aug. 6, 2018.

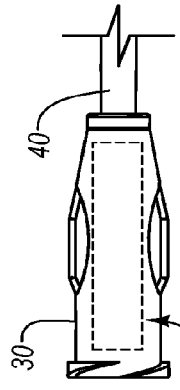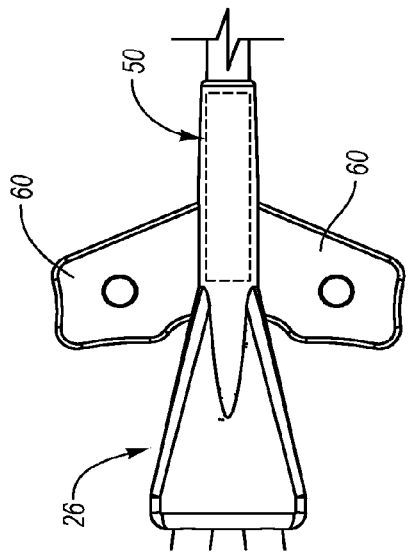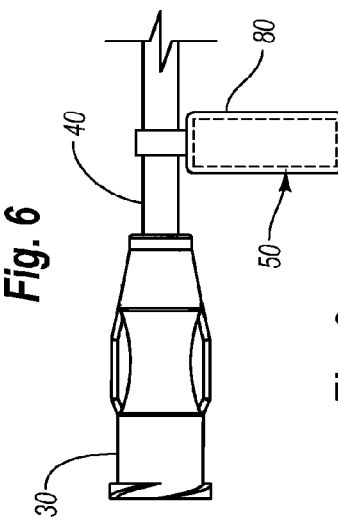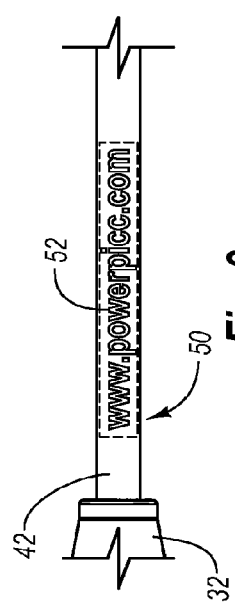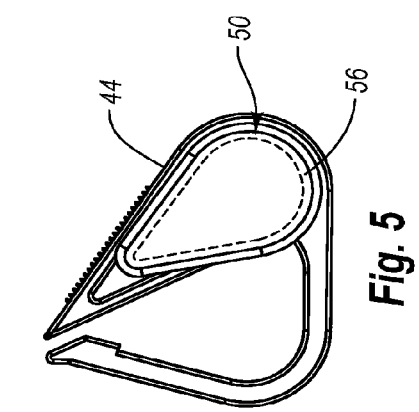

RESOURCE INFORMATION KEY FOR AN INSERTABLE MEDICAL DEVICE

CROSS-REFERENCE TO RELATED APPLICATION

This application is a division of U.S. patent application Ser. No. 11/937,302, filed Nov. 8, 2007, now U.S. Pat. No. 9,642,986, which claims the benefit of the U.S. Provisional Application No. 60/864,806, filed Nov. 8, 2006, and titled "Medical Device Uniform Resource Identifier," each of which is incorporated herein by reference in its entirety.

TECHNOLOGY FIELD

The present invention generally relates to medical devices insertable into the body of a patient. In particular, embodiments of the present invention relate to a system by which a key for directing a user to resource information relating to the medical device is included on the device in a manner that enables the resource information to be readily accessed.

BRIEF SUMMARY

Manufacturers of medical devices, including those configured for insertion into the body of a patient, generally make every effort to ensure that each device is accompanied by a comprehensive collection of printed and other material intended to ensure that the device is placed and used correctly. Examples of such devices include peripherally inserted central catheters ("PICCs"), dialysis catheters, peripheral catheters, and other devices designed to enable intravascular access to the patient.

Despite the above-mentioned efforts, however, situations may arise where further information regarding a particular medical device is desired or needed in order for the device to be properly employed. For instance, the accompanying medical device documentation may be misplaced or lost, or further information may be released after the device was manufactured and distributed. Such information may be needed by the practitioner placing the medical device in the patient, or by the patient or caregiver after device insertion. In these or other cases, it may be difficult for the practitioner, patient, or caregiver to readily acquire needed information relating to the device.

In light of the above discussion, therefore, a need exists for a solution that overcomes the above-identified challenges relating to the availability of medical device information for insertable medical devices.

The present invention has been developed in response to the above and other needs in the art. Briefly summarized, embodiments of the present invention are directed to a system by which resource information relating to an insertable medical device, such as an intravascular catheter, can be identified by its source so as to be accessed by a practitioner, caregiver, or patient. In particular, a resource information key is included at a predetermined key location on or proximate to the medical device, wherein the key indicates the source of the resource information.

In one example embodiment, therefore, an insertable medical device for establishing intravascular access to a patient, such as a peripherally inserted central catheter ("PICC"), is disclosed and comprises: an internal portion configured for intravascular insertion into the patient, and a portion external to the patient. The exterior portion of the PICC includes a resource information key that is positioned at a predetermined key location. The resource information key indicates a website where a user can acquire the resource information relating to the medical device.

These and other features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof that are illustrated in the appended drawings. It is appreciated that these drawings depict only typical embodiments of the invention and are therefore not to be considered limiting of its scope. The invention will be described and explained with additional specificity and detail through the use of the accompanying drawings in which:

FIG. 3 is a close-up top view of a portion of the PICC of FIG. 2, showing further details of the resource information key;

FIG. 4 is a top view of a connector portion of the PICC of FIG. 2, showing a resource information key location according to one embodiment;

FIG. 5 is a top view of a clamp portion of the PICC of FIG. 2, showing a resource information key location according to one embodiment;

FIG. 6 is a top view of a bifurcation hub portion of the PICC of FIG. 2, showing a resource information key location according to one embodiment;

FIG. 7 is a top view of a catheter portion of the PICC of FIG. 2, showing a resource information key location according to one embodiment;

FIG. 8 is a top view of a portion of the PICC of FIG. 2, including a hang tag having a resource information key location according to one embodiment;

DETAILED DESCRIPTION OF SELECTED EMBODIMENTS

Reference will now be made to figures wherein like structures will be provided with like reference designations. It is understood that the drawings are diagrammatic and schematic representations of exemplary embodiments of the invention, and are not limiting of the present invention nor are they necessarily drawn to scale.

FIGS. 1-10 depict various features of embodiments of the present invention, which is generally directed to a system by which resource information relating to an insertable medical device, such as an intravascular catheter device, can be identified so as to be accessed by a practitioner, caregiver, or patient.

Figure 1:
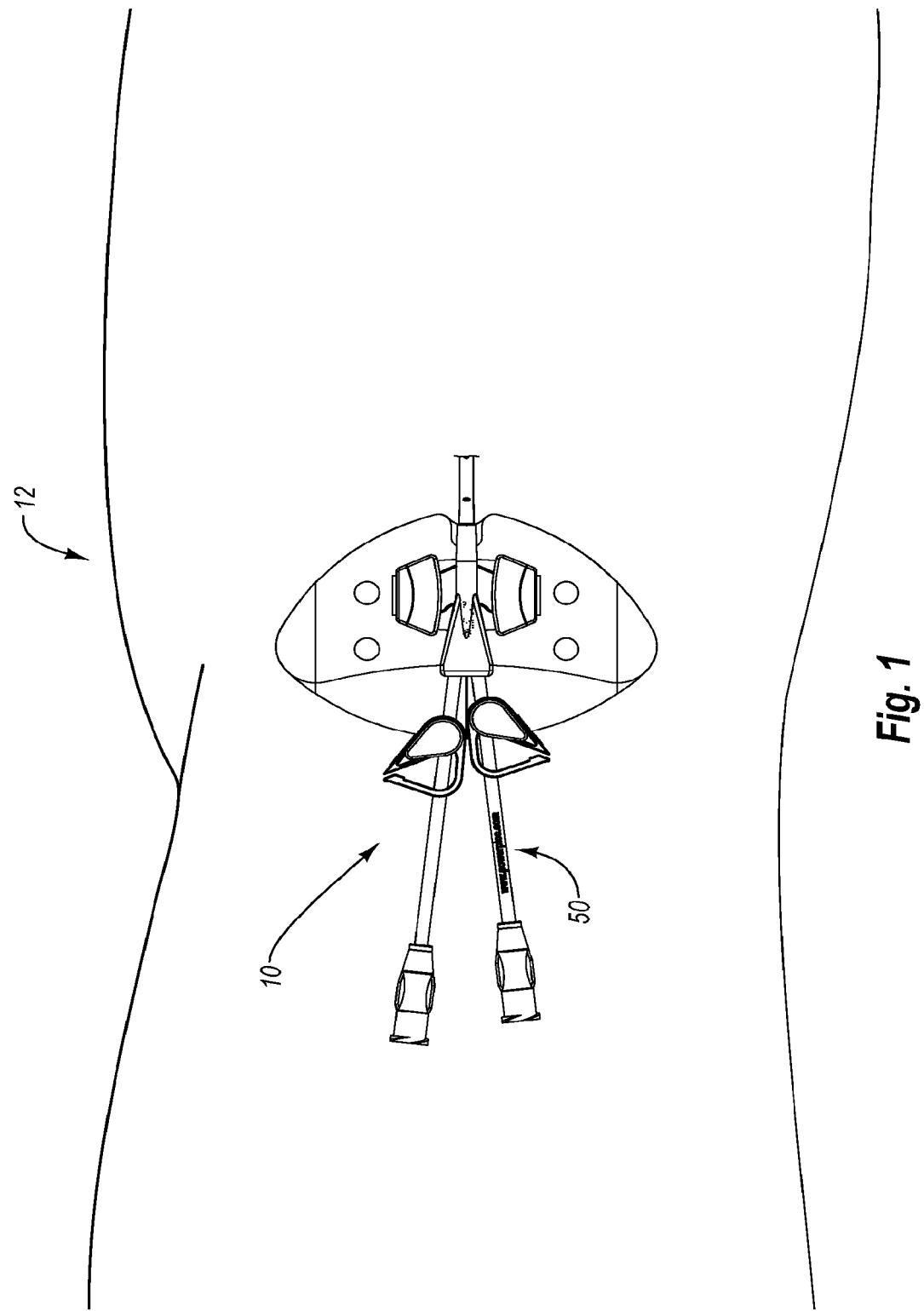
FIG. 1 is a top view of a peripherally inserted central catheter ("PICC") partially inserted in the arm of a patient, thereby depicting one example of an insertable medical device that benefits from the present invention according to one embodiment thereof.

Reference is first made to FIG. 1, which depicts a medical device, generally designated at 10, that is configured for insertion into a body 12 of a patient. In particular, the medical device 10 depicted in FIG. 1 is a dual lumen peripherally inserted central catheter ("PICC"), and is shown inserted in the arm of the patient body 12. Also shown in FIG. 1 is a resource information key location, to be described more fully below, generally indicated at 50.

It should be noted that, though the accompanying drawings depict a PICC device, other medical devices that are at least partially inserted into the patient can also benefit from the principles of the present invention to be described herein. Examples of such devices include dialysis catheters, peripheral catheters, cannulas, infusion sets, and other devices designed to enable intravascular access to the patient. In yet other embodiments, completely implantable devices, such as subcutaneous access ports, can also employ embodiments of the present invention. As such, the breadth of the present invention should not be construed as being limited to the medical devices explicitly depicted and described herein.

Figure 2:
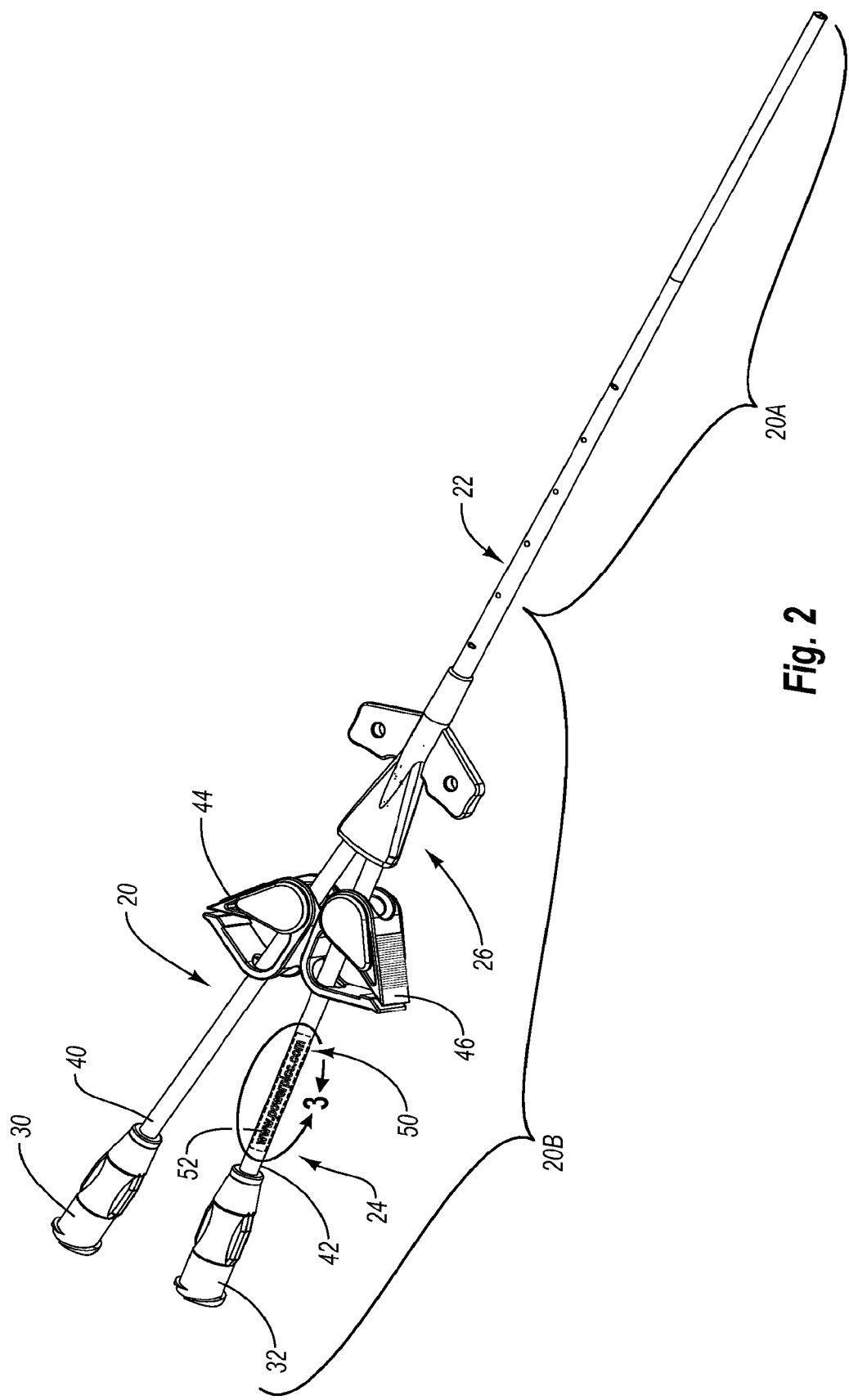
FIG. 2 is a perspective view of the PICC of FIG. 1 before insertion into a patient, including a resource information key according to one embodiment.

Reference is now made to FIG. 2, depicting in further detail the PICC shown in FIG. 1 before placement in a patient, here shown at 20. Comparison of FIG. 2 with FIG. 1 will reveal that the PICC 20 includes an internal portion 20A for insertion into the vasculature of a patient and an external portion 20B that remains outside of the body of the patient during PICC use. As embodiments of the present invention can be applied to other insertable medical devices, the internal and external portions of other devices would be varied according to the particular design of the insertable medical device. As shown, the PICC 20 generally includes a catheter 22, an extension leg assembly 24, and a bifurcation hub 26 that operably interconnects the catheter to the extension leg assembly.

In further detail, the extension leg assembly 24 is configured to enable the infusion or aspiration of fluids to or from the patient vasculature via the catheter 22 and bifurcation hub 26. The extension leg assembly 24 includes a first connector 30 and second connector 32 that are connected to a first extension tube 40 and a second extension tube 42, respectively. A first clamp 44 is included on the first extension tube 40, and a second clamp 46 is included on the second extension tube 42. Note that more or fewer extension tubes could be included with the PICC 20.

In accordance with one embodiment, a key is provided with the PICC 20 to enable further information relating to the PICC to be accessed by a patient, practitioner, caregiver, etc. Specifically, a resource information key location ("RIKL"), generally indicated at 50, is provided on the PICC 20. The RIKL 50 defines an area of the PICC 20 where a resource information key 52 is located. As will be described, the resource information key 52 provides data to one as to a source where further information regarding the PICC 20 can be accessed. Not providing the information itself, it instead acts as a "key," enabling further PICC-related information to be located.

The contents of the resource information key 52 can be any alpha-numeric, typographical, graphical content or other visual indicia that can visually convey to the user the source where further information regarding the medical device can be found. As such, letters, numbers, graphical or other symbols, etc. may be used alone or in combination to form the resource information key 52. In yet another embodiment, the key could be identified not visually, but rather by palpation.

For example, and as shown in greater detail in FIG. 3, the resource information key 52 in one embodiment is implemented as a website uniform resource locator ("URL"), www.powerpicc.com, where a user can access via the Internet various web pages giving further information regarding the structure, use, precautions, or other aspects relating to the PICC 20. Such information may be beneficial to the user, or may be critical in order to ensure patient safety, especially in instances where printed material that originally accompanied the PICC 20 has been misplaced or lost, or when new information has become available regarding the PICC.

In light of the above discussion, it is appreciated that in accordance with embodiments of the present invention the resource information key 52 can take one of several forms, especially with regard to pointing the user to an Internet-based resource. As such, examples of a resource information key include a web address, URL, URI, IP address, etc., which in turn direct the user to a location on the Internet where the further information may be found. Of course, the content of the resource information key 52 can be varied according to the device on which it is found.

As shown in FIGS. 2 and 3, the resource information key 52 is included in the RIKL 50, which in turn is disposed on a portion of the second extension tube 42. Generally, the RIKL 50 is chosen so as to be easily viewable by the user. The RIKL 50 should also be sized large enough for the resource information key 52 to be read without undue effort. Generally, locations proximally disposed on the external portion of the medical device are advantageous so as to enable the key to be readily viewed. However, as will be seen in the additional example embodiments to be discussed below, the key may be located at a variety of locations on the medical device. The resource information key 52 can be defined on the RIKL 50 in a variety of ways, including etching, embossing, labeling, ink or other printing, etc.

As mentioned, though it is located on the second extension tube 42 in the embodiments shown in FIGS. 1-3, the resource location key in other embodiments can be positioned at other resource information key locations on the PICC or other insertable medical device. FIGS. 4-8 give various examples of such alternative placement locations for the resource information key. In FIG. 4, for example, the RIKL 50 is disposed on the first connector 30 of the extension leg assembly 24, while FIG. 5 shows the RIKL disposed on a cap 56 affixed to the first clamp 44.

In FIG. 6, the RIKL 50 is disposed on an axial portion of the bifurcation hub 26. Alternatively, the RIKL can be disposed on one or both of two suture wings 60 extending from the body of the bifurcation hub 26. In FIG. 7, the RIKL 50 is disposed on a proximal portion 22A of the catheter 22 that is not inserted into the patient. In FIG. 8, a hang tag 80 or other attachable component can be added to the PICC 20 to include the RIKL 50 thereon.

Figure 9:
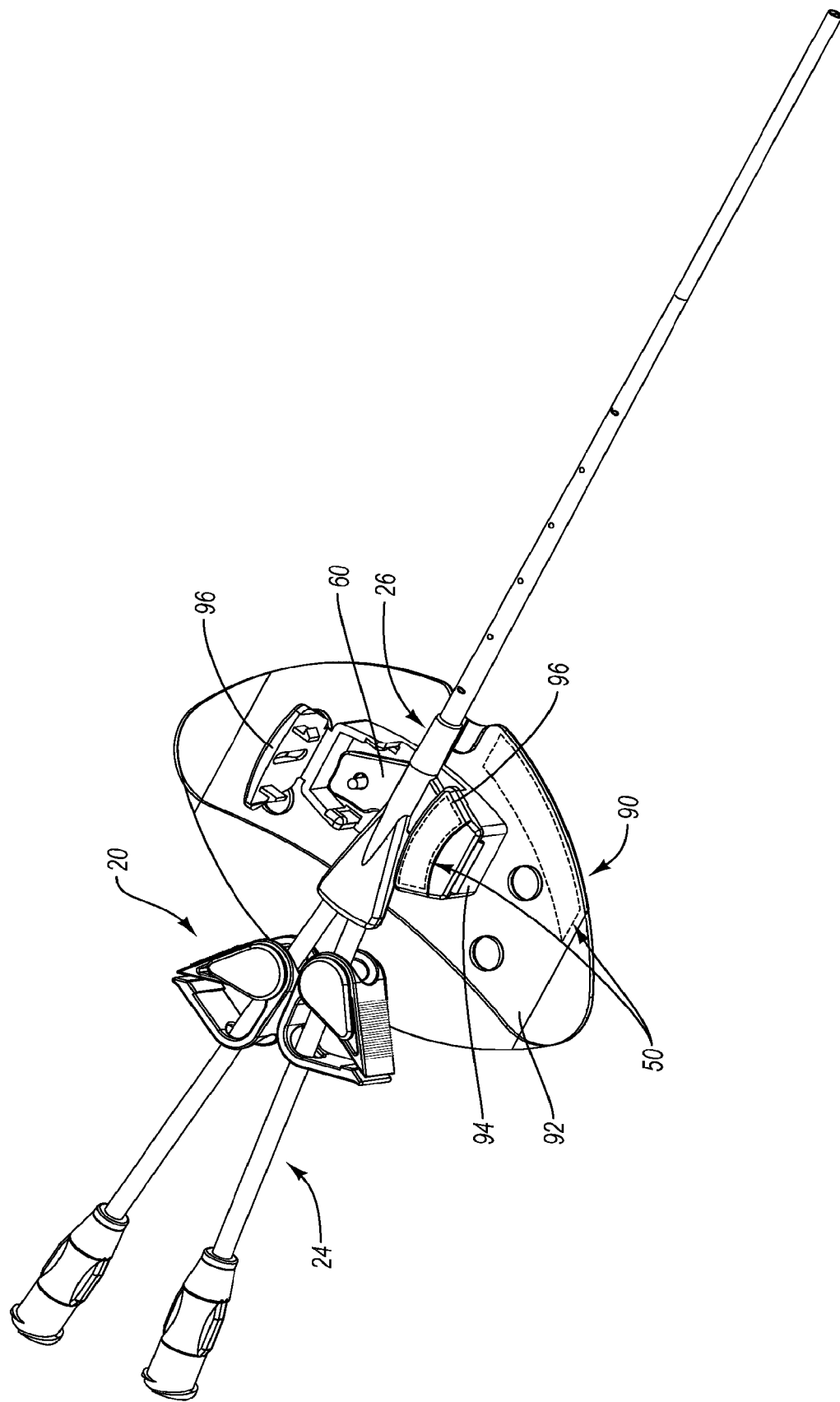
FIG. 9 is a perspective view of a PICC coupled with a stabilization device having a plurality of resource information key locations according to one embodiment.

The embodiments shown in FIGS. 1-8 depict the RIKL 50 disposed on a portion of the PICC 20 itself. However, the RIKL may also be positioned on a component that is not part of, but typically used in conjunction with, the PICC 20 or other insertable medical device. In FIG. 9, for example, a catheter stabilization device sold under the trademark STAT-LOCK® is shown at 90 and is commonly used to assist in securing the PICC 20 in place after insertion into the patient vasculature. The stabilization device 90 includes a base 92 and a retention assembly 94 for retaining the bifurcation hub 26 of the PICC 20. The retention assembly 94 includes selectively closeable lids 96. FIG. 9 further shows two possible areas for the RIKL 50: on a portion of the device base 92, and on one or both of the lids 96. Other areas could, of course, be employed on the stabilization device 90 for positioning the RIKL 50.

Figure 10:
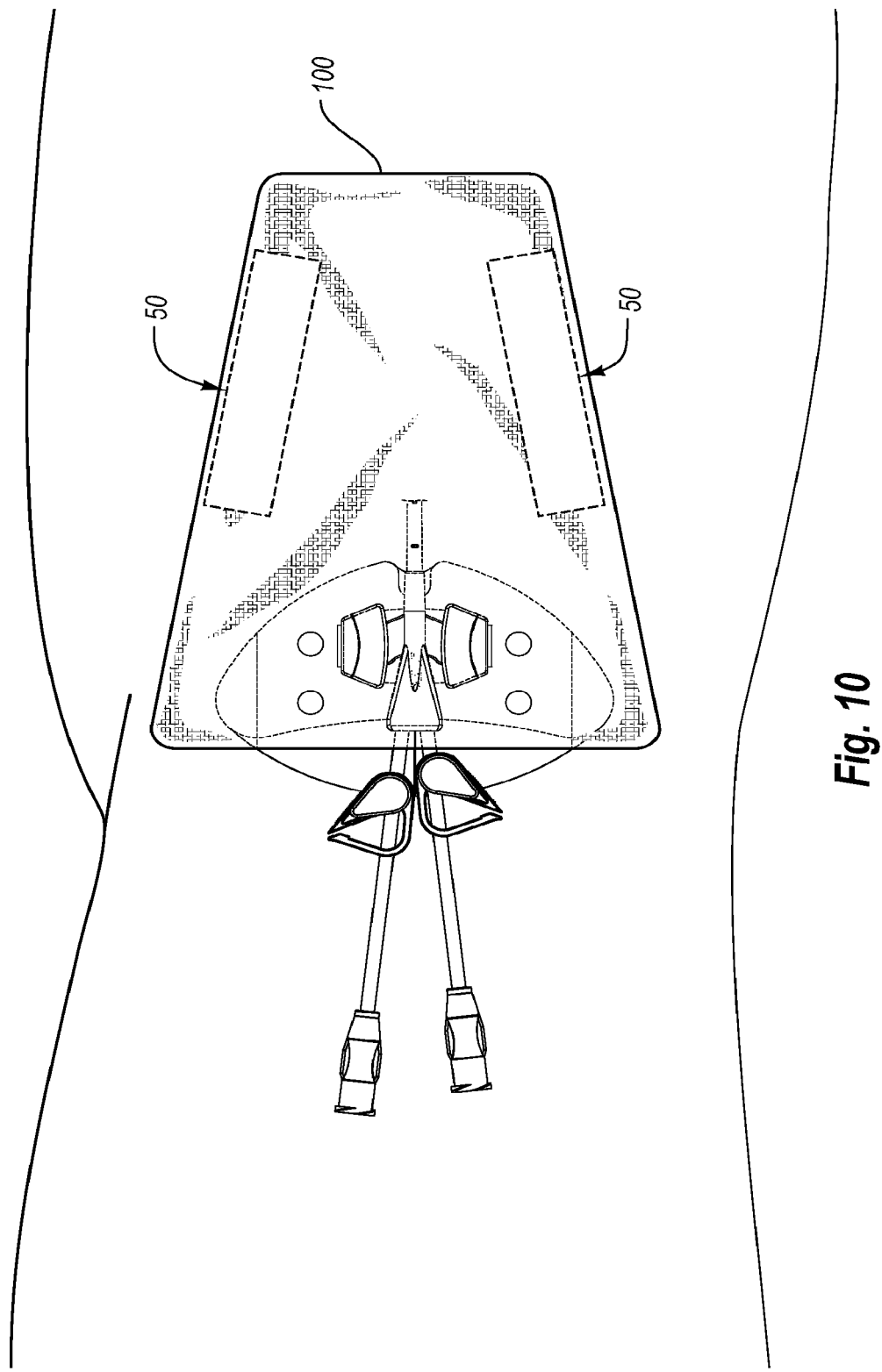
FIG. 10 is a top view of a PICC and stabilization device together with a dressing having a plurality of resource information key locations according to one embodiment of the present invention.

FIG. 10 shows an adhesive dressing 100 that is commonly used to cover a portion of the PICC 20 and stabilization device 90 for increased hygiene. The dressing 100 here includes two RIKLs 50 as yet another example of possible locations for placement of the resource information key. It is appreciated that, in addition to the examples discussed above, many other key locations could be devised on a variety of insertable medical devices, including devices that are fully implanted in the patient body, such as access ports, if desired. The present invention should not therefore be limited to only what is explicitly shown and described herein.

Figure 11:
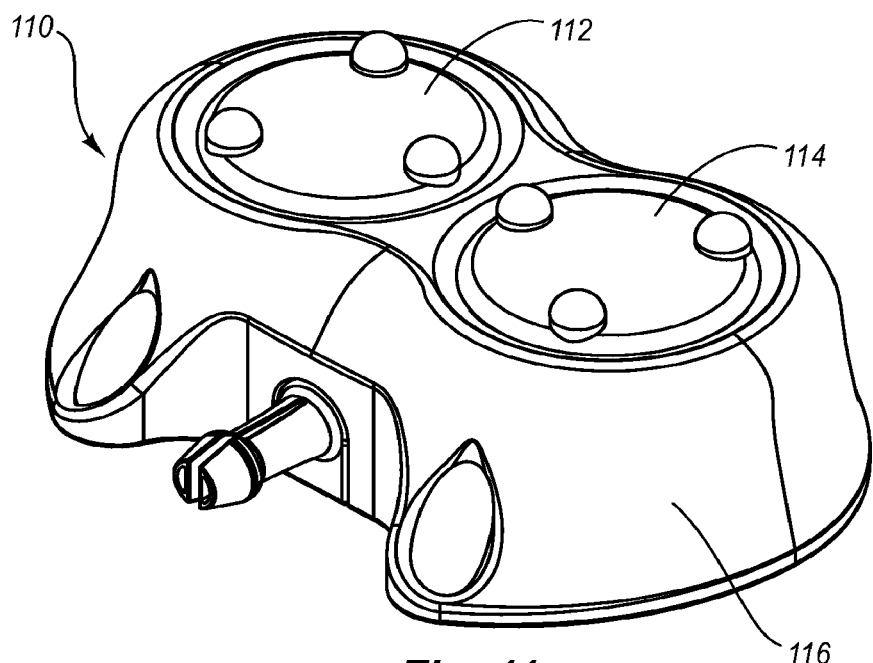
FIG. 11 is a perspective view of a dual septum implantable access port, depicting an example of an implantable medical device that benefits from the present invention according to one embodiment thereof.
Figure 12:
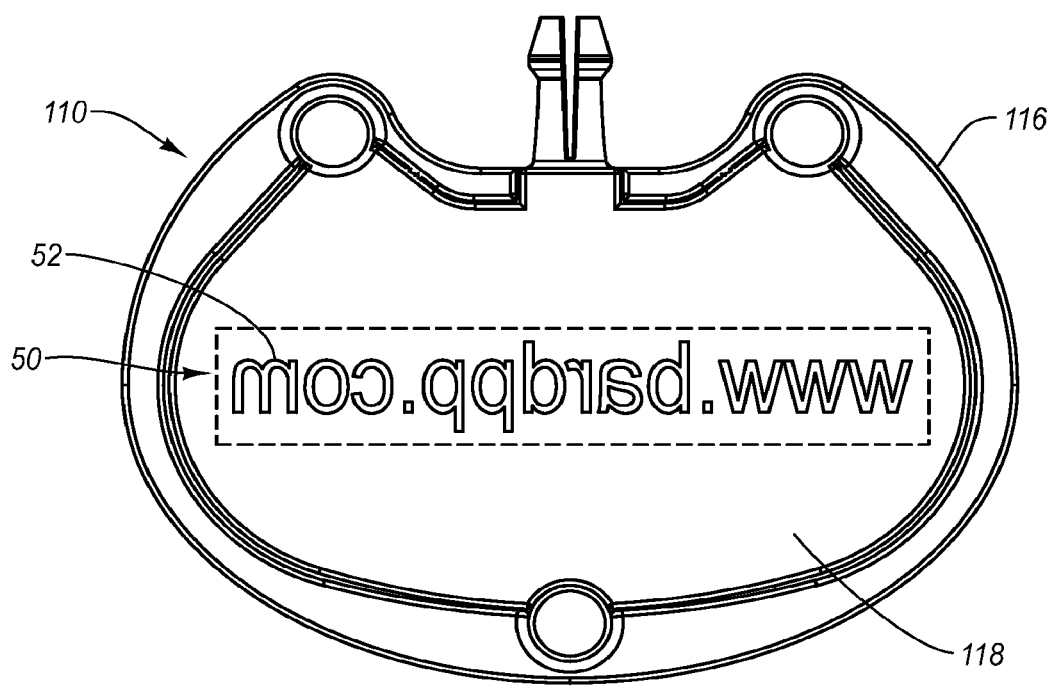
FIG. 12 is a bottom view of the dual septum implantable access port of FIG. 11, including a reversed radiopaque resource information key according to one embodiment of the present invention.

FIGS. 11 and 12 depict the present invention as employed in yet another example embodiment. In particular, FIGS. 11 and 12 depict a dual-septum access port 110 configured for subcutaneous implantation into the body of a patient. The access port 110 includes a first septum 112 covering a first reservoir, and a second septum 114 covering a second reservoir. The reservoirs are defined by a body 116. The resource information key 52 is disposed at a predetermined resource information key location 50 on a bottom surface 118 of the access port body 116.

The key 52 in FIG. 12, "www.bardpp.com," is positioned on the bottom surface 118 in an inverse, or mirror-image, configuration. Further, the material used to define the key 52 includes a radiopaque material such that the key 52 is visible when a radiographic, or x-ray, image is taken of the implanted access port 110. The inverse key 52 in this case will appear non-inverse when the x-ray image is viewed, thus allowing the orientation of the implanted access port to be readily ascertained. Of course, the key may be positioned in any one of a variety of configurations, inverse or not, and locations on the access port.

The content of the key 52 can also serve to identify the access port 110 in terms of type, size, manufacturer, etc., if desired. In addition, the key 52 provides a source to which an observer can go to access further information regarding the access port 110, as in previous embodiments. Note that, while shown here in connection with a dual-septum access port, single-septum or otherwise configured access ports, as well as other types of implantable medical devices, can also benefit from the principles described herein with regard to the present embodiment.

The present invention may be embodied in other specific forms without departing from its spirit or essential characteristics. The described embodiments are to be considered in all respects only as illustrative, not restrictive. The scope of the invention is, therefore, indicated by the appended claims rather than by the foregoing description. All changes that come within the meaning and range of equivalency of the claims are to be embraced within their scope.

What is claimed is:

1. A medical method, comprising:
    providing a peripherally inserted central catheter access line comprising:
        an internal portion including a catheter designed for intravascular insertion into a patient; and
        an external portion designed to remain outside of the patient;
    positioning a visible internet-based resource information key at a predetermined key location on the external portion;
    inserting the internal portion into the patient;
    viewing the internet-based resource information key on the external portion;
    accessing the internet and entering the internet-based resource information key; and
    acquiring information about the peripherally inserted central catheter access line.

2. The medical method according to claim 1, wherein the positioning comprises selecting the external portion from the group consisting of an extension tube, a connector, a clamp, a hub, a proximal portion of the catheter, and combinations thereof.

3. The medical method according to claim 1, wherein the positioning is an application method selected from the group consisting of etching, embossing, labeling, printing with ink, and combinations thereof.

4. The medical method according to claim 1, wherein the positioning comprises attaching a component to the external portion.

5. A medical method, comprising:
    providing a peripherally inserted central catheter access line comprising:
        an internal portion including a catheter designed for intravascular insertion into a patient;
        an external portion configured to remain outside of the patient; and
        a catheter stabilization device designed to secure the peripherally inserted central catheter access line in position;
    positioning a visible internet-based resource information key at a predetermined key location on the catheter stabilization device;
    inserting the internal portion into the patient;
    viewing the internet-based resource information key on the external portion;
    accessing the internet and entering the internet-based resource information key; and
    acquiring information about the peripherally inserted central catheter access line.

6. The medical method according to claim 5, wherein the catheter stabilization device comprises an adhesive dressing designed to cover a section of the external portion, the positioning comprising positioning the visible internet-based resource information key on the adhesive dressing.

* * * * *